United States Patent [19]
Neal et al.

[11] Patent Number: 5,858,759
[45] Date of Patent: Jan. 12, 1999

[54] D-N-CARBAMOYL-AMINO ACID AMIDOHYDROLASE AND HYDANTOINASE

[75] Inventors: Robert John Neal, Brighton; Alison Michelle Griffin, Worthing; Hazel Claire Gorham, Abingdon, all of England

[73] Assignee: SmithKline Beecham p.l.c., Brentford, United Kingdom

[21] Appl. No.: 815,356

[22] Filed: Mar. 11, 1997

Related U.S. Application Data

[63] Continuation of Ser. No. 356,369, Dec. 23, 1994, abandoned.

[30] Foreign Application Priority Data

Jun. 30, 1992 [GB] United Kingdom ............ 9213855
Jun. 30, 1992 [GB] United Kingdom ............ 9213857

[51] Int. Cl.⁶ .................. C12N 1/21; C12N 9/78; C12N 9/86; C12N 15/63
[52] U.S. Cl. ............ 435/227; 435/231; 435/320.1; 435/325; 435/252.2; 435/252.33; 536/23.2
[58] Field of Search ............... 536/23.2; 435/227, 435/231, 320.1, 325, 252.3, 252.33, 254.11

[56] References Cited

U.S. PATENT DOCUMENTS

| | | | |
|---|---|---|---|
| 4,312,948 | 1/1982 | Olivieri et al. | 435/106 |
| 4,418,146 | 11/1983 | Lungershausen et al. | 435/106 |
| 4,912,044 | 3/1990 | Jacob et al. | 435/172.3 |
| 4,956,282 | 9/1990 | Goodman et al. | 435/69.51 |
| 5,565,344 | 10/1996 | Nanba et al. | 435/106 |

FOREIGN PATENT DOCUMENTS

| | | |
|---|---|---|
| 0 219 034 | 4/1987 | European Pat. Off. |
| 515 698 | 12/1992 | European Pat. Off. |
| 2 022 581 | 12/1979 | United Kingdom |
| WO 92/10579 | 6/1992 | WIPO |

OTHER PUBLICATIONS

Rurser et al., Biotechnol. Lett. 12:259–264 (1990).
Syldatk et al., Adv. Biochem. Engineering/Biotechnol. 41:29–75 (1990).
*Patent Abstracts of Japan*, 12 No. 230 [C–508][3077] (1988).
Runser, et al., "Properties of the Hydantoinase from Agrobacterium", *Chemical Abstracts*, 113 No. 107 (1990): Abs. 147669k.
Kitagawa, et. al., "Novel Hydantionase", *Chemical Abstracts*, 104 No. 23 (1986): Abs. 205546v.
Olivieri, et al., "Microbial Transformation of Racemic Hydantoins to D–Amino Acids", *Biotechnology and Bioengineering* XXIII, pp. 2173–2183 (1981).

*Primary Examiner*—Eric Grimes
*Attorney, Agent, or Firm*—Elizabeth J. Hecht; Alissa M. Eagle; William T. King

[57] ABSTRACT

Processes are provided for the production of a carbamoylase enzyme which has the capability of converting a D-N-carbamoyl (optionally substituted phenyl) glycine by expressing recombinant DNA encoding a carbamoylase in a homologous host. Also provided are specific recombinant DNA vectors producing high levels of expression of the carbamoylase enzyme and/or hydantoinase enzyme in homologous and heterologous hosts and their use in the production of D-α amino acids.

45 Claims, 28 Drawing Sheets

AGATCTGGCAGTACCTCTAGCTCCTCGATCACGCTATCAGTCGGATCGAGCACGATGATA
|___|    ^10       ^20       ^30       ^40       ^50       ^60
BglII

TGGTAGCCGTAGTCGATCGCCGACTTGCCGCCGGCCATGCCGTCCCATTTGGCGACCGCC
    ^70       ^80       ^90       ^100      ^110      ^120

TCCCTCAGGCTATGGCCGCGGTCCTGCTGGCAGAAATCGACGATGGTCGTCGTGCCGCCA
    ^130      ^140      ^150      ^160      ^170      ^180

CAGGCGGCGCGACCGTCGCGGTTGCGAATGTGTCGGCCGACTGCGTGTTGAAGCTGACCG
    ^190      ^200      ^210      ^220      ^230      ^240

TCTCGACATGCGTATGAACGTCGATGCCGCCCGGAAAAACGTAGCGGCCGGAGGCGTCGA
    ^250      ^260      ^270      ^280      ^290      ^300

TTTGTCCGGCCGGCCGGGCCGAACGTTCCGCCGATCTGGGCGATCTTGCCATCCTTGATT
    ^310      ^320      ^330      ^340      ^350      ^360

CCGAGATCGGCGGGAGAAATCCCGTCCGCGGTTACGATGGTTCCGTTCTTGATGATGATA
    ^370      ^380      ^390      ^400      ^410     |  ^420
                                                      EcoRV—

TCCATAAAGCAGCTCTCAGGGTTGATGGATAAATTCTATATGCGGTATGATGTTCTTTAT
_|  ^430      ^440      ^450      ^460      ^470      ^480

ATAAAGTTTTCATGTTGCCTTGTATCTGTCAAGCGGGAAGGGAAGTTCTCCGGAATCGGC
    ^490      ^500      ^510      ^520      ^530      ^540

GCTGCGAGGGAACGTATCGAGTTTCGATTAGACGCGGTTGAAAGCGAGCGGTCATTGAAT
    ^550      ^560      ^570      ^580      ^590      ^600

ACGGAACCTCTGCCAACCCTATTCGGCGAGCTGGATTTTTTCTTCTCGTTCGCGAGCTCC
    ^610      ^620      ^630      ^640      ^650|     |^660
                                                  SacI

TAAAACGGCGCCGTTCAATCCGGGTGAAAAAGTTCAACCATCGGAAATTTTGACCCTGGT
    ^670      ^680      ^690      ^700      ^710      ^720

CCTTGACAGATCAAAAGTTTTACGCCTGTAGTATGAGTACTGCATGTGGCATTTATCCTT
    ^730      ^740      ^750      ^760      ^770      ^780

TTTGTAGAACAATCATTGGCGTGCCAAGCTGAGACGTGTGTTCCTGAAATGTGCATAGC
    ^790      ^800      ^810      ^820      ^830

Fig. IOA

```
                                                                  MetThrArg
AGCGTTCTCCCGGCCGCGAGGCCGGATTAACTATCGAAGGAGCAAAGGTTCATGACACGT
     ^849      ^859      ^869      ^879      [^889    ]  ^899
                                              └─BspHI┘

GlnMetIleLeuAlaValGlyGlnGlnGlyProIleAlaArgAlaGluThrArgGluGln
CAGATGATACTTGCTGTCGGACAGCAAGGCCCCATCGCGCGAGCGGAGACACGCGAACAG
     ^909      ^919      ^929      ^939      ^949      ^959

ValValGlyArgLeuLeuAspMetLeuThrAsnAlaAlaSerArgGlyValAsnPheIle
GTGGTTGGCCGCCTCCTCGACATGTTGACGAACGCAGCCAGCCGGGGCGTGAACTTCATC
     ^969      ^979      ^989      ^999      ^1009     ^1019

ValPheProGluLeuAlaLeuThrThrPhePheProArgTrpHisPheThrAspGluAla
GTCTTTCCCGAGCTTGCGCTCACGACCTTCTTCCCGCGCTGGCATTTCACCGACGAGGCC
     ^1029     ^1039     ^1049     ^1059     ^1069     ^1079

GluLeuAspSerPheTyrGluThrGluMetProGlyProValValArgProLeuPheGlu
GAGCTCGATAGCTTCTATGAGACCGAAATGCCCGGCCCGGTGGTCCGTCCACTCTTTGAG
[   ] ^1089     ^1099     ^1109     ^1119     ^1129     ^1139
└SacI┘

ThrAlaAlaGluLeuGlyIleGlyPheAsnLeuGlyTyrAlaGluLeuValValGluGly
ACGGCCGCCGAACTCGGGATCGGCTTCAATCTGGGCTACGCCGAACTCGTCGTCGAAGGC
     ^1149     ^1159     ^1169     ^1179     ^1189     ^1199

GlyValLysArgArgPheAsnThrSerIleLeuValAspLysSerGlyLysIleValGly
GGCGTCAAGCGTCGCTTCAACACGTCCATTCTGGTGGATAAGTCAGGCAAGATCGTCGGC
     ^1209     ^1219     ^1229     ^1239     ^1249     ^1259

LysTyrArgLysIleHisLeuProGlyHisLysGluTyrGluAlaTyrArgProPheGln
AAGTATCGTAAGATCCATTTGCCGGGTCACAAGGAGTACGAGGCCTACCGGCCGTTCCAG
     ^1269     ^1279     ^1289     ^1299     ^1309     ^1319

HisLeuGluLysArgTyrPheGluProGlyAspLeuGlyPheProValTyrAspValAsp
CATCTTGAAAAGCGTTATTTCGAGCCGGGCGATCTCGGCTTCCCGGTCTATGACGTCGAC
     ^1329     ^1339     ^1349     ^1359     ^1369[   ]^1379
                                                  └SalI┘

AlaAlaLysMetGlyMetPheIleCysAsnAspArgArgTrpProGluThrTrpArgVal
GCCGCGAAAATGGGGATGTTCATCTGCAACGATCGCCGCTGGCCTGAAACGTGGCGGGTG
     ^1389     ^1399     ^1409     ^1419     ^1429     ^1439

MetGlyLeuLysGlyAlaGluIleIleCysGlyGlyThrAsnThrProThrHisAsnPro
ATGGGACTTAAGGGCGCCGAGATCATCTGCGGCGGCTACAACACGCCGACCCACAATCCC
     ^1449     ^1459     ^1469     ^1479     ^1489     ^1499

ProValProGlnHisAspHisLeuThrSerPheHisHisLeuLeuSerMetGlnAlaGly
CCCGTTCCCCAGCACGACCATCTGACGTCGTTCCACCACCTTCTGTCGATGCAGGCCGGG
     ^1509     ^1519     ^1529     ^1539     ^1549     ^1559

SerTyrGlnAsnGlyAlaTrpSerAlaAlaAlaGlyLysValGlyMetGluGluGlyCys
TCGTACCAAAACGGCGCCTGGTCCGCGGCGGCCGGCAAGGTCGGCATGGAGGAGGGGTGC
     ^1569     ^1579     ^1589     ^1599     ^1609   [ ^1619
                                                     └SphI─
```

Fig. 10B-1

```
MetLeuLeuGlyHisSerCysIleValAlaProThrGlyGluIleValAlaLeuThrThr
ATGCTGCTCGGCCATTCGTGCATCGTGGCGCCGACCGGCGAAATCGTTGCCCTGACCACG
     ^1629      ^1639      ^1649      ^1659      ^1669      ^1679

ThrLeuGluAspGluValIleThrAlaAlaValAspLeuAspArgCysArgGluLeuArg
ACGTTGGAAGACGAGGTGATCACCGCCGCCGTCGATCTCGACCGCTGCCGGGAACTGCGC
     ^1689      ^1699      ^1709      ^1719      ^1729      ^1739

GluHisIlePheAsnPheLysAlaHisArgGlnProGlnHisTyrGlyLeuIleAlaGlu
GAACACATCTTCAATTTCAAAGCCCATCGTCAGCCACAGCACTACGGTCTGATCGCGGAA
     ^1749      ^1759      ^1769      ^1779      ^1789      ^1799
                                                            └EcoRI─

Phe***
TTCTGAAGGTCAGGCCAAAAAAACGGATGGGGCTGGGGACGTCGAAGCGGCAGCGTTACG
     ^1809      ^1819      ^1829      ^1839      ^1849      ^1859

CCTATCCGATCGAGAAAGCTT
     ^1869   ^1879
           └HindIII
```

Fig. IOB-2

5,858,759

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1880 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 891..1805

( x i ) SEQUENCE DESCRIPTION: SEQ ID NO:1:

```
AGATCTGGCA  GTACCTCTAG  CTCCTCGATC  ACGCTATCAG  TCGGATCGAG  CACGATGATA      60

TGGTAGCCGT  AGTCGATCGC  CGACTTGCCG  CCGGCCATGC  CGTCCCATTT  GGCGACCGCC     120

TCCCTCAGGC  TATGGCCGCG  GTCCTGCTGG  CAGAAATCGA  CGATGGTCGT  CGTGCCGCCA     180

CAGGCGGCGC  GACCGTCGCG  GTTGCGAATG  TGTCGGCCGA  CTGCGTGTTG  AAGCTGACCG     240

TCTCGACATG  CGTATGAACG  TCGATGCCGC  CCGGAAAAAC  GTAGCGGCCG  GAGGCGTCGA     300

TTTGTCCGGC  CGGCCGGGCC  GAACGTTCCG  CCGATCTGGG  CGATCTTGCC  ATCCTTGATT     360

CCGAGATCGG  CGGGAGAAAT  CCCGTCCGCG  GTTACGATGG  TTCCGTTCTT  GATGATGATA     420

TCCATAAAGC  AGCTCTCAGG  GTTGATGGAT  AAATTCTATA  TGCGGTATGA  TGTTCTTTAT     480

ATAAAGTTTT  CATGTTGCCT  TGTATCTGTC  AAGCGGGAAG  GGAAGTTCTC  CGGAATCGGC     540

GCTGCGAGGG  AACGTATCGA  GTTTCGATTA  GACGCGGTTG  AAAGCGAGCG  GTCATTGAAT     600

ACGGAACCTC  TGCCAACCCT  ATTCGGCGAG  CTGGATTTTT  TCTTCTCGTT  CGCGAGCTCC     660

TAAAACGGCG  CCGTTCAATC  CGGGTGAAAA  AGTTCAACCA  TCGGAAATTT  TGACCCTGGT     720

CCTTGACAGA  TCAAAAGTTT  TACGCCTGTA  GTATGAGTAC  TGCATGTGGC  ATTTATCCTT     780

TTTGTAGAAC  AATCATTGGC  GTGCCAAGCT  GAGACGTGTG  TTCCTGAAAT  GTGCATAGCA     840

GCGTTCTCCC  GGCCGCGAGG  CCGGATTAAC  TATCGAAGGA  GCAAAGGTTC  ATG  ACA        896
                                                            Met  Thr
                                                              1

CGT  CAG  ATG  ATA  CTT  GCT  GTC  GGA  CAG  CAA  GGC  CCC  ATC  GCG  CGA  GCG     944
Arg  Gln  Met  Ile  Leu  Ala  Val  Gly  Gln  Gln  Gly  Pro  Ile  Ala  Arg  Ala
          5                        10                       15

GAG  ACA  CGC  GAA  CAG  GTG  GTT  GGC  CGC  CTC  CTC  GAC  ATG  TTG  ACG  AAC     992
Glu  Thr  Arg  Glu  Gln  Val  Val  Gly  Arg  Leu  Leu  Asp  Met  Leu  Thr  Asn
     20                       25                       30

GCA  GCC  AGC  CGG  GGC  GTG  AAC  TTC  ATC  GTC  TTT  CCC  GAG  CTT  GCG  CTC    1040
Ala  Ala  Ser  Arg  Gly  Val  Asn  Phe  Ile  Val  Phe  Pro  Glu  Leu  Ala  Leu
35                       40                       45                       50

ACG  ACC  TTC  TTC  CCG  CGC  TGG  CAT  TTC  ACC  GAC  GAG  GCC  GAG  CTC  GAT    1088
Thr  Thr  Phe  Phe  Pro  Arg  Trp  His  Phe  Thr  Asp  Glu  Ala  Glu  Leu  Asp
                    55                       60                       65

AGC  TTC  TAT  GAG  ACC  GAA  ATG  CCC  GGC  CCG  GTG  GTC  CGT  CCA  CTC  TTT    1136
```

```
Ser  Phe  Tyr  Glu  Thr  Glu  Met  Pro  Gly  Pro  Val  Val  Arg  Pro  Leu  Phe
          70                       75                            80

GAG  ACG  GCC  GCC  GAA  CTC  GGG  ATC  GGC  TTC  AAT  CTG  GGC  TAC  GCC  GAA      1184
Glu  Thr  Ala  Ala  Glu  Leu  Gly  Ile  Gly  Phe  Asn  Leu  Gly  Tyr  Ala  Glu
          85                       90                            95

CTC  GTC  GTC  GAA  GGC  GGC  GTC  AAG  CGT  CGC  TTC  AAC  ACG  TCC  ATT  CTG      1232
Leu  Val  Val  Glu  Gly  Gly  Val  Lys  Arg  Arg  Phe  Asn  Thr  Ser  Ile  Leu
          100                      105                           110

GTG  GAT  AAG  TCA  GGC  AAG  ATC  GTC  GGC  AAG  TAT  CGT  AAG  ATC  CAT  TTG      1280
Val  Asp  Lys  Ser  Gly  Lys  Ile  Val  Gly  Lys  Tyr  Arg  Lys  Ile  His  Leu
115                      120                      125                      130

CCG  GGT  CAC  AAG  GAG  TAC  GAG  GCC  TAC  CGG  CCG  TTC  CAG  CAT  CTT  GAA      1328
Pro  Gly  His  Lys  Glu  Tyr  Glu  Ala  Tyr  Arg  Pro  Phe  Gln  His  Leu  Glu
               135                      140                           145

AAG  CGT  TAT  TTC  GAG  CCG  GGC  GAT  CTC  GGC  TTC  CCG  GTC  TAT  GAC  GTC      1376
Lys  Arg  Tyr  Phe  Glu  Pro  Gly  Asp  Leu  Gly  Phe  Pro  Val  Tyr  Asp  Val
               150                      155                           160

GAC  GCC  GCG  AAA  ATG  GGG  ATG  TTC  ATC  TGC  AAC  GAT  CGC  CGC  TGG  CCT      1424
Asp  Ala  Ala  Lys  Met  Gly  Met  Phe  Ile  Cys  Asn  Asp  Arg  Arg  Trp  Pro
               165                      170                      175

GAA  ACG  TGG  CGG  GTG  ATG  GGA  CTT  AAG  GGC  GCC  GAG  ATC  ATC  TGC  GGC      1472
Glu  Thr  Trp  Arg  Val  Met  Gly  Leu  Lys  Gly  Ala  Glu  Ile  Ile  Cys  Gly
          180                      185                      190

GGC  TAC  AAC  ACG  CCG  ACC  CAC  AAT  CCC  CCC  GTT  CCC  CAG  CAC  GAC  CAT      1520
Gly  Tyr  Asn  Thr  Pro  Thr  His  Asn  Pro  Pro  Val  Pro  Gln  His  Asp  His
195                      200                      205                      210

CTG  ACG  TCC  TTC  CAC  CAC  CTT  CTG  TCG  ATG  CAG  GCC  GGG  TCG  TAC  CAA      1568
Leu  Thr  Ser  Phe  His  His  Leu  Leu  Ser  Met  Gln  Ala  Gly  Ser  Tyr  Gln
               215                      220                           225

AAC  GGC  GCC  TGG  TCC  GCG  GCG  GCC  GGC  AAG  GTC  GGC  ATG  GAG  GAG  GGG      1616
Asn  Gly  Ala  Trp  Ser  Ala  Ala  Ala  Gly  Lys  Val  Gly  Met  Glu  Glu  Gly
          230                      235                           240

TGC  ATG  CTG  CTC  GGC  CAT  TCG  TGC  ATC  GTG  GCG  CCG  ACC  GGC  GAA  ATC      1664
Cys  Met  Leu  Leu  Gly  His  Ser  Cys  Ile  Val  Ala  Pro  Thr  Gly  Glu  Ile
          245                      250                      255

GTT  GCC  CTG  ACC  ACG  ACG  TTG  GAA  GAC  GAG  GTG  ATC  ACC  GCC  GCC  GTC      1712
Val  Ala  Leu  Thr  Thr  Thr  Leu  Glu  Asp  Glu  Val  Ile  Thr  Ala  Ala  Val
260                      265                      270

GAT  CTC  GAC  CGC  TGC  CGG  GAA  CTG  CGC  GAA  CAC  ATC  TTC  AAT  TTC  AAA      1760
Asp  Leu  Asp  Arg  Cys  Arg  Glu  Leu  Arg  Glu  His  Ile  Phe  Asn  Phe  Lys
275                      280                      285                      290

GCC  CAT  CGT  CAG  CCA  CAG  CAC  TAC  GGT  CTG  ATC  GCG  GAA  TTC  TGA           1805
Ala  His  Arg  Gln  Pro  Gln  His  Tyr  Gly  Leu  Ile  Ala  Glu  Phe   *
               295                      300                      305

AGGTCAGGCC  AAAAAAACGG  ATGGGGCTGG  GGACGTCGAA  GCGGCAGCGT  TACGCCTATC            1865

CGATCGAGAA  AGCTT                                                                  1880
```

(2) INFORMATION FOR SEQ ID NO:2:

(i) SEQUENCE CHARACTERISTICS:
        (A) LENGTH: 304 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Thr  Arg  Gln  Met  Ile  Leu  Ala  Val  Gly  Gln  Gln  Gly  Pro  Ile  Ala
1                   5                        10                       15

Arg  Ala  Glu  Thr  Arg  Glu  Gln  Val  Val  Gly  Arg  Leu  Leu  Asp  Met  Leu
               20                       25                       30
```

-continued

| | | | | | | | | | | | | | | |
|---|---|---|---|---|---|---|---|---|---|---|---|---|---|---|
| Thr | Asn | Ala | Ala | Ser | Arg | Gly | Val | Asn | Phe | Ile | Val | Phe | Pro | Glu | Leu |
| | | 35 | | | | | 40 | | | | | 45 | | | |
| Ala | Leu | Thr | Thr | Phe | Phe | Pro | Arg | Trp | His | Phe | Thr | Asp | Glu | Ala | Glu |
| | 50 | | | | | 55 | | | | | 60 | | | | |
| Leu | Asp | Ser | Phe | Tyr | Glu | Thr | Glu | Met | Pro | Gly | Pro | Val | Val | Arg | Pro |
| 65 | | | | | 70 | | | | | 75 | | | | | 80 |
| Leu | Phe | Glu | Thr | Ala | Ala | Glu | Leu | Gly | Ile | Gly | Phe | Asn | Leu | Gly | Tyr |
| | | | | 85 | | | | | 90 | | | | | 95 | |
| Ala | Glu | Leu | Val | Val | Glu | Gly | Gly | Val | Lys | Arg | Arg | Phe | Asn | Thr | Ser |
| | | | 100 | | | | | 105 | | | | | 110 | | |
| Ile | Leu | Val | Asp | Lys | Ser | Gly | Lys | Ile | Val | Gly | Lys | Tyr | Arg | Lys | Ile |
| | | 115 | | | | | 120 | | | | | 125 | | | |
| His | Leu | Pro | Gly | His | Lys | Glu | Tyr | Glu | Ala | Tyr | Arg | Pro | Phe | Gln | His |
| | 130 | | | | | 135 | | | | | 140 | | | | |
| Leu | Glu | Lys | Arg | Tyr | Phe | Glu | Pro | Gly | Asp | Leu | Gly | Phe | Pro | Val | Tyr |
| 145 | | | | | 150 | | | | | 155 | | | | | 160 |
| Asp | Val | Asp | Ala | Ala | Lys | Met | Gly | Met | Phe | Ile | Cys | Asn | Asp | Arg | Arg |
| | | | | 165 | | | | | 170 | | | | | 175 | |
| Trp | Pro | Glu | Thr | Trp | Arg | Val | Met | Gly | Leu | Lys | Gly | Ala | Glu | Ile | Ile |
| | | | 180 | | | | | 185 | | | | | 190 | | |
| Cys | Gly | Gly | Tyr | Asn | Thr | Pro | Thr | His | Asn | Pro | Pro | Val | Pro | Gln | His |
| | | 195 | | | | | 200 | | | | | 205 | | | |
| Asp | His | Leu | Thr | Ser | Phe | His | His | Leu | Leu | Ser | Met | Gln | Ala | Gly | Ser |
| | 210 | | | | | 215 | | | | | 220 | | | | |
| Tyr | Gln | Asn | Gly | Ala | Trp | Ser | Ala | Ala | Ala | Gly | Lys | Val | Gly | Met | Glu |
| 225 | | | | | 230 | | | | | 235 | | | | | 240 |
| Glu | Gly | Cys | Met | Leu | Leu | Gly | His | Ser | Cys | Ile | Val | Ala | Pro | Thr | Gly |
| | | | | 245 | | | | | 250 | | | | | 255 | |
| Glu | Ile | Val | Ala | Leu | Thr | Thr | Thr | Leu | Glu | Asp | Glu | Val | Ile | Thr | Ala |
| | | | 260 | | | | | 265 | | | | | 270 | | |
| Ala | Val | Asp | Leu | Asp | Arg | Cys | Arg | Glu | Leu | Arg | Glu | His | Ile | Phe | Asn |
| | | 275 | | | | | 280 | | | | | 285 | | | |
| Phe | Lys | Ala | His | Arg | Gln | Pro | Gln | His | Tyr | Gly | Leu | Ile | Ala | Glu | Phe |
| | 290 | | | | | 295 | | | | | 300 | | | | |
| * | | | | | | | | | | | | | | | |
| 305 | | | | | | | | | | | | | | | |

D-N-CARBAMOYL-AMINO ACID AMIDOHYDROLASE AND HYDANTOINASE

This is a continuation of application Ser. No. 08/356,369, filed Dec. 23, 1994, now abandoned.

The present invention relates to DNA molecules and to recombinant vectors for use in the transformation of a microbial host. In particular, the invention relates to DNA encoding a carbamoylase enzyme and to hosts transformed with recombinant vectors comprising the said DNA.

Certain D-α-amino acids are well known pharmaceutical intermediates. For example D(–) p-hydroxyphenylglycine is used as a starting material for the production of the antibiotic amoxycillin. Processes for the preparation of D-α-amino acids are therefore of importance and several enzymatic processes enabling production of D-product from racemic starting material have been reported.

U.K. patents 1,534,426 and 1,564,982, for example, disclose hydantoinase producing organisms which will hydrolyse 5-(substituted phenyl)hydantoins to give intermediate D-N-carbamoyl-(substituted phenyl)glycines. However, to obtain the corresponding D-α-amino acid it is necessary subsequently to hydrolyse the N-carbamoyl compounds formed, for example with nitrous acid.

To overcome the problem of having a first enzymatic and a second chemical step to prepare D-α-amino acids from hydantoin starting material it is possible to convert the N-carbamoyl intermediate into the α-amino acid enzymatically with a carbamoylase enzyme produced by a microorganism, e.g. an Agrobacterium species as described in U.K. Patent No.2,022,581. A drawback with Agrobacterium NRRL B11291 described in U.K. Patent No. 2,022,581, however, is that only limited amounts of carbamoylase enzyme are produced. In addition, the organism exhibits other enzyme activity which may be undesirable in certain circumstances.

PCT application WO 92/10579 (Kanegafuchi) discloses the production of D α amino acids using bacteria transformed with recombinant DNA encoding a carbamoylase enzyme which converts D-N-carbamoyl-α-amino acid to a D-α amino acid.

We have found that surprisingly higher levels of enzyme activity can be obtained when a carbamoylase gene is expressed in a homologous host. By 'homologous host' we mean that the host is the same type of organism from which the gene was originally isolated.

Accordingly the present invention provides a process for the production of a carbamoylase enzyme which has the capability of converting a D-N-carbamoyl (optionally substituted phenyl)glycine into the corresponding D-(optionally substituted phenyl)glycine by expressing recombinant DNA encoding a carbamoylase gene in a homologous host.

Preferably the homologous host is Agrobacterium ie the carbamoylase gene is derived from Agrobacterium.

We have additionally found that particular constructs lead to high levels of expression in both heterologous and homologous hosts.

Accordingly in a further aspect of the present invention there is also provided a recombinant DNA vector comprising a gene encoding a carbanoylase enzyme which has the capability of converting a D-N-carbamoyl (optionally substituted phenyl)glycine into the corresponding D-(optionally substituted phenyl)glycine wherein the DNA vector is selected from the group consisting of pCAR1, pCAR6, pCAR12, pCAR21, pCAR26, pCAR 27, pCAR28, pCAR29, pGal2789RS3Carb, p CAR31, pCAR32, pCAR36, pCAR44 and pCAR46 as herein described.

The advantage of the invention is that particularly large quantities of the carbamoylase enzyme can be produced. Under suitable conditions active carbamoylase enzyme can thus be obtained and used, preferably immobilised on a solid support, to prepare the chosen D-α-amino acid.

Suitable substituents for optionally substituted phenyl groups as described herein include hydroxy, $C_{(1-6)}$alkyl, $C_{(1-6)}$ alkoxy and halogen. Preferred (substituted phenyl) glycines include (p-hydroxyphenyl)glycine and (3,4-dihydroxyphenyl)glycine, especially (p-hydroxyphenyl) glycine.

The carbamoylase gene may be isolated, as described hereinbelow, from total or chromosomal DNA of organisms which produce a carbamoylase enzyme having the said capability.

The carbamoylase gene may comprise further genes, for example regulatory elements, or flanking DNA which has no particular or known function.

In a related aspect the invention provides DNA comprising a gene encoding a hydantoinase enzyme which has the ability to convert a D,L-(optionally substituted phenyl) hydantoin into the corresponding D-N-carbamoyl (optionally substituted phenyl) glycine.

It will of course, be understood that the DNA of the invention has been separated from the majority of such chromosomal DNA and is not in its 'natural' state, i.e. the form in which it occurs in nature. In one aspect, the DNA of the invention is in isolated and substantially purified form and/or consists essentially of a hydantoinase gene encoding the said hydantoinase enzyme.

In a further aspect the invention provides recombinant DNA comprising the DNA of the invention.

Preferably the recombinant DNA encoding the hydantoinase gene comprises a recombinant vector, more preferably a high expression vector capable of expressing high levels of gene transcript.

The invention further provides a process for transforming a host cell with a recombinant vector encoding the carbamoylase or hydantoinase enzyme according to the invention which comprises mixing together the host and recombinant vector under conventional transformation or electroporation conditions.

In another aspect of the invention there is provided a host cell transformed with a recombinant vector according to the invention. Suitable hosts include Agrobacterium and *E. coli.*, for example *E. coli* DH1, *E. coli* JM 101 and *E. coli* HB 101.

The invention also encompasses culturing the transformed host according to the invention so that production of the carbamoylase or hydantoinase enzyme takes place.

In a further aspect of the invention there is provided isolated and recombinant DNA encoding a gene for a carbamoylase enzyme and a gene for a hydantoinase enzyme. Culture of a suitable transformed host can then produce both carbamoylase and hydantoinase activity.

Advantageous results are obtained when the carbamoylase and hydantoinase activity are provided in the same construct for example as in pCAR1, pCAR6, pCAR31, PCAR32 and pCAR36.

In one aspect the DNA of the invention is obtained from a microorganism, preferably from a soil isolate designated '80/44-2A' as described herein. The isolate '80/44-2A' is believed to be an Agrobacterium and whilst we do not wish to be bound by this designation the strain will herein be referred to as Agrobacterium 80/44-2A. DNA obtained therefrom will similarly be referred to as Agrobacterium DNA.

In order to define the invention more clearly reference is made to the accompanying drawings in which:

FIG. 1 shows a restriction site and function map of plasmid pCP19;

Abbn:

B=BglII, Ba=BamHI, E=EcoRI, H=HindIII, P=Pst I, C=Cla I, S=Sal I, Tc$^R$=Tetracycline resistance gene, cos=cos site from bacteriophage lambda, Solid line represents DNA from pCP19;

Figure 4:
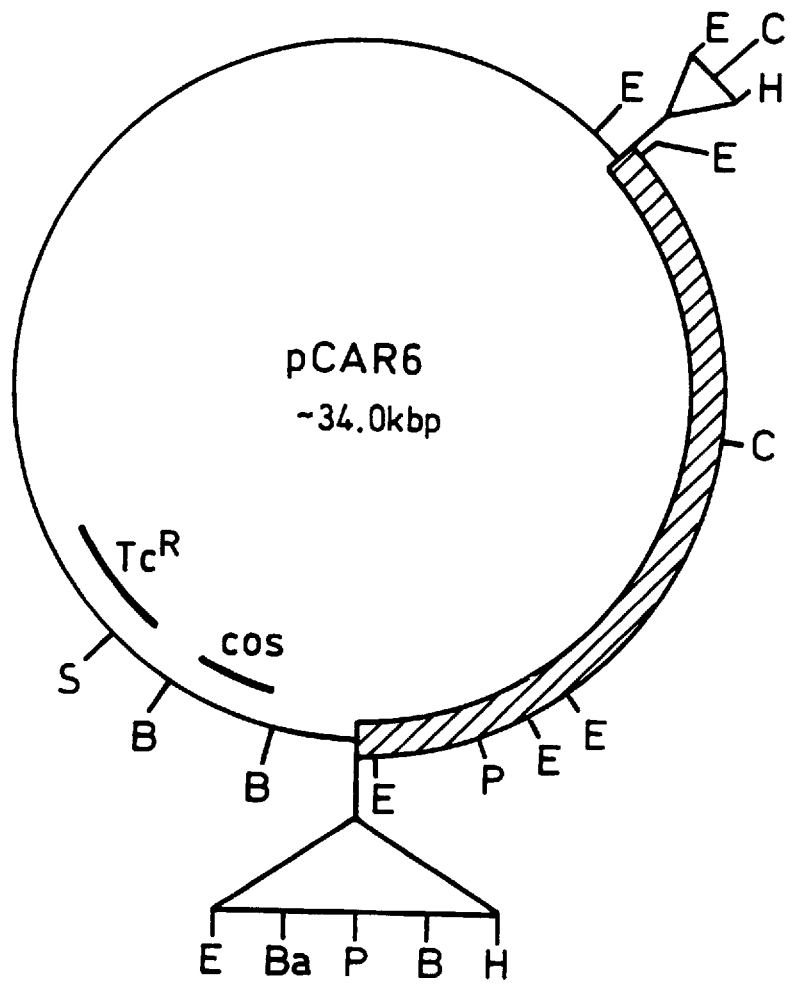
Figure 5:
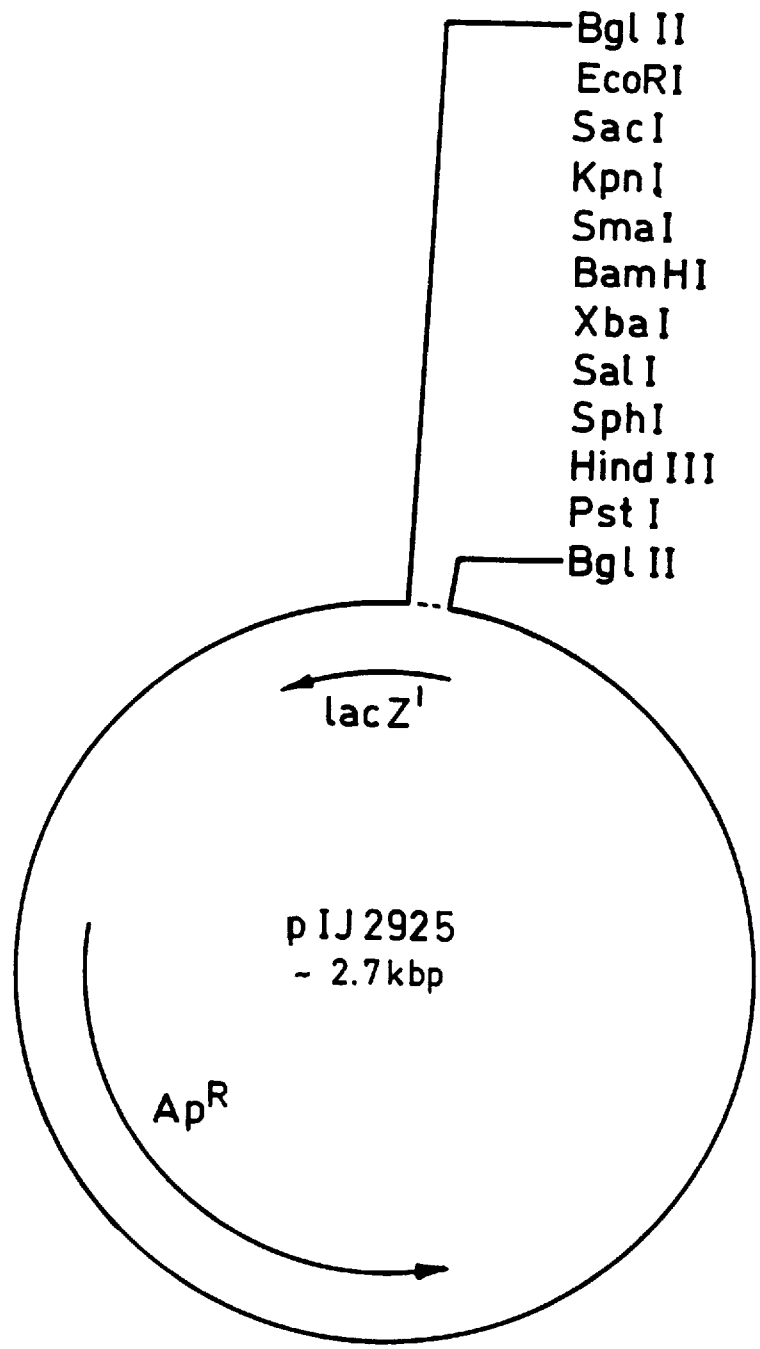

Abbn:

C=Cla I, B=Bgl II, Ba=Bam HI, E=EcoRI, H=Hind III, P=Pst I, (Only E,H, and P. enzymes have been used for mapping of the Arobacterium DNA), S=Sal I, Tc$^R$=Tetracycline resistance gene, cos=cos site from bacteriophage lambda, Solid line represents DNA from pCP19, Shaded portion represents DNA from Agrobacterium 80/44-2A FIG. 4 shows a restriction site and function map of plasmid pCAR6;

Abbn:

C=Cla I, B=Bgl II, Ba=Bam HI, H=Hind III, E=EcoRI, P=Pst I (Only E,H, and P. enzymes have been used mapping the insert in this plasmid (and Cla I), S=Sal I, Solid line represents DNA from pCP19, Shaded portion represents DNA from Agrobacterium FIG. 5 shows a restriction site and function map of plasmid pIJ2925;

Abbn:

Ap$^R$=ampicillin resistance

Figure 6:
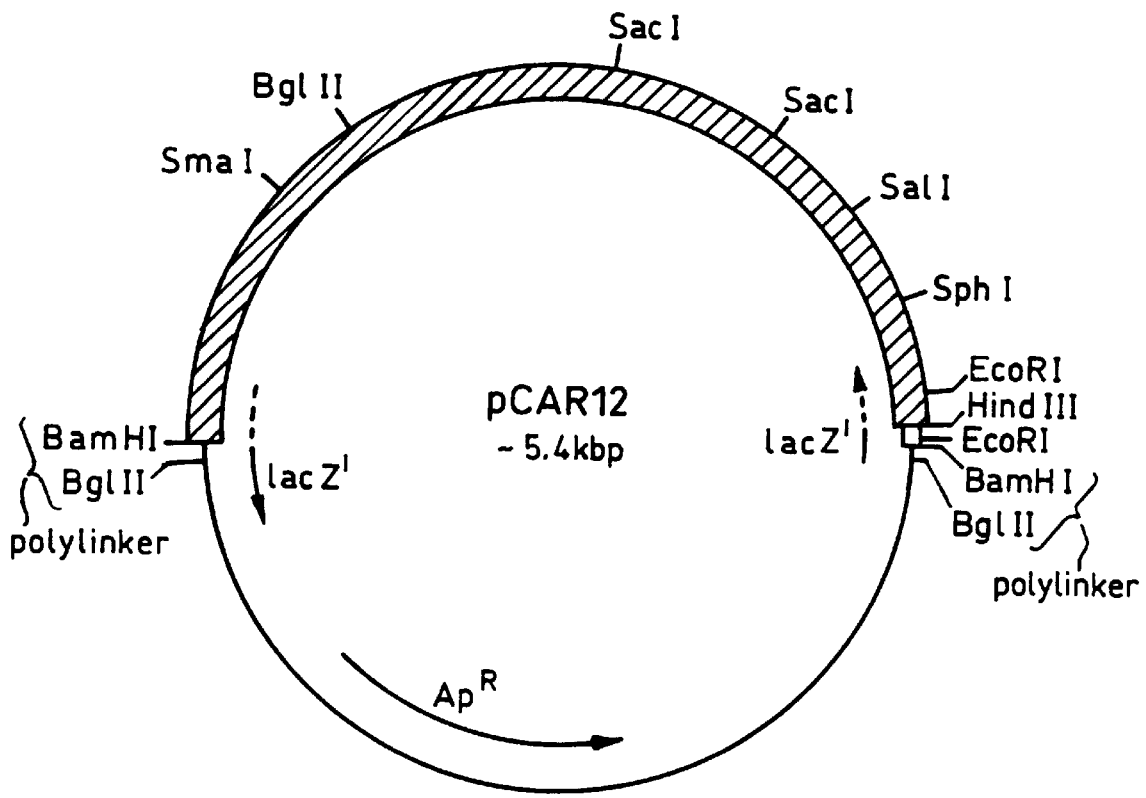

FIG. 6 shows a restriction site and function map of plasmid pCAR12; In the regions marked "polylinker", not all of the restriction sites in the pIJ2925 DNA are shown.

Figure 7:
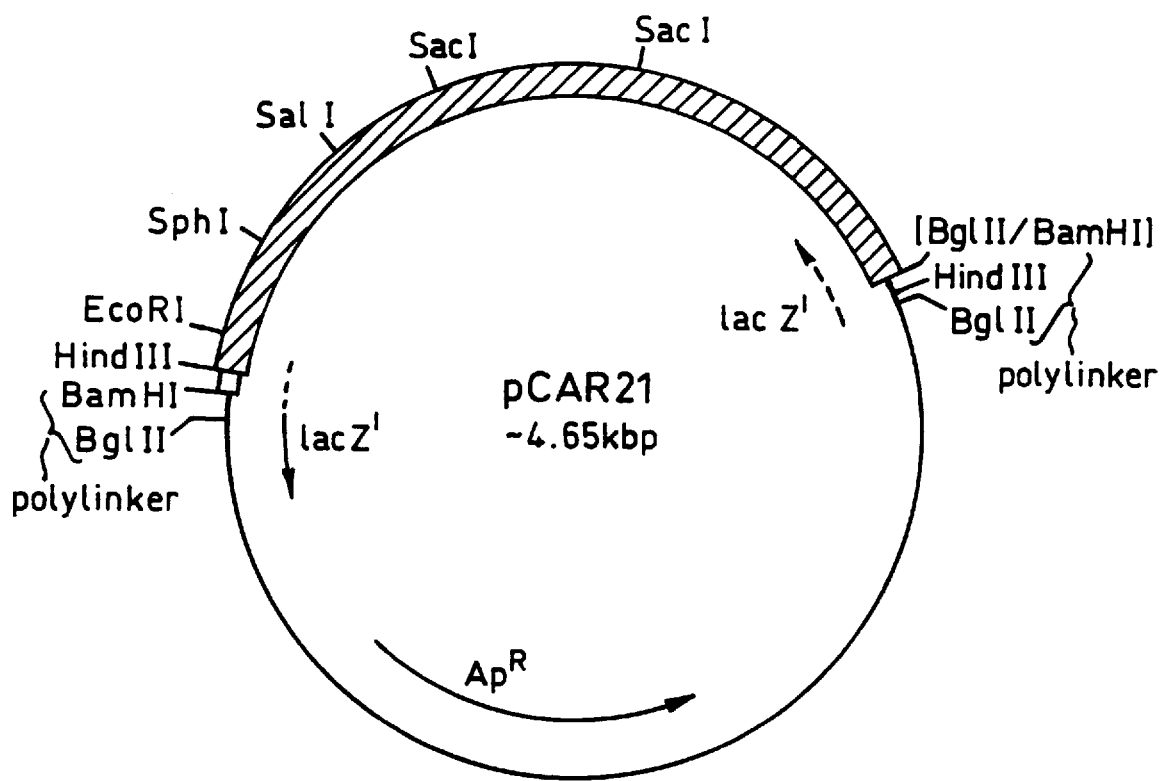

Abbn:

Non-shaded portion represents pCP19 DNA (cloned from pCAR6 together with Agrobacterium DNA), Shaded portion represents Agrobacterium DNA, Solid line represents pIJ2925 DNA FIG. 7 shows a restriction site and function map of plasmid pCAR21; In the regions marked "polylinker", not all of the restriction sites in the pIJ2925 DNA are shown.

Figure 8:
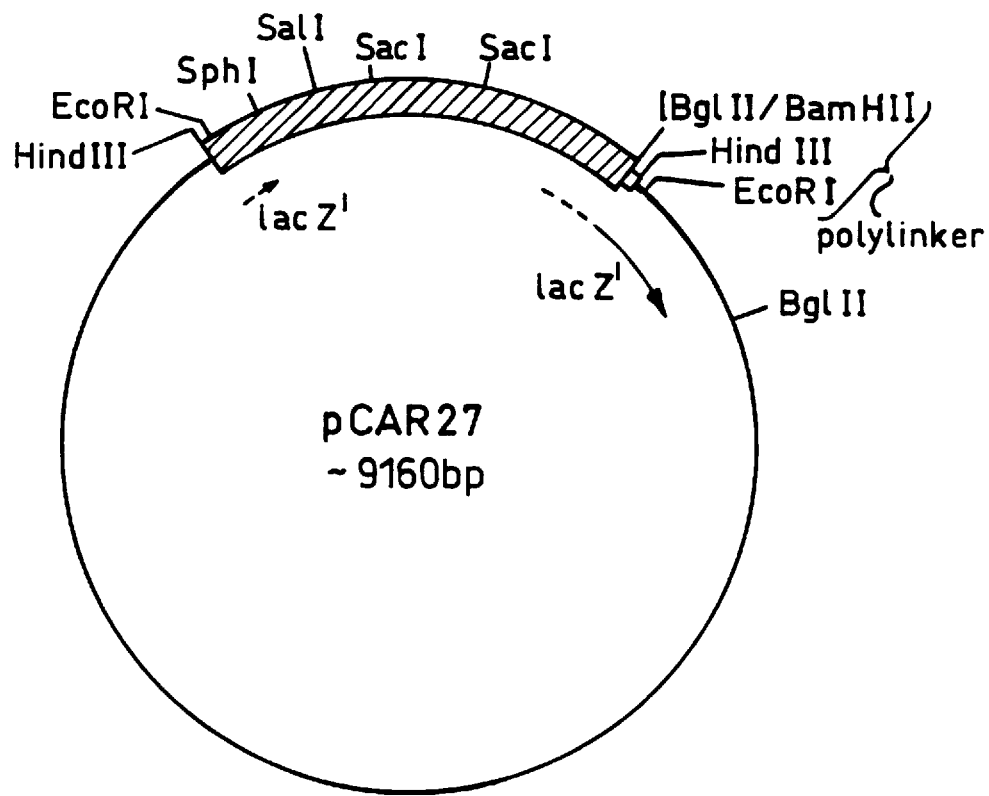
Figure 9:
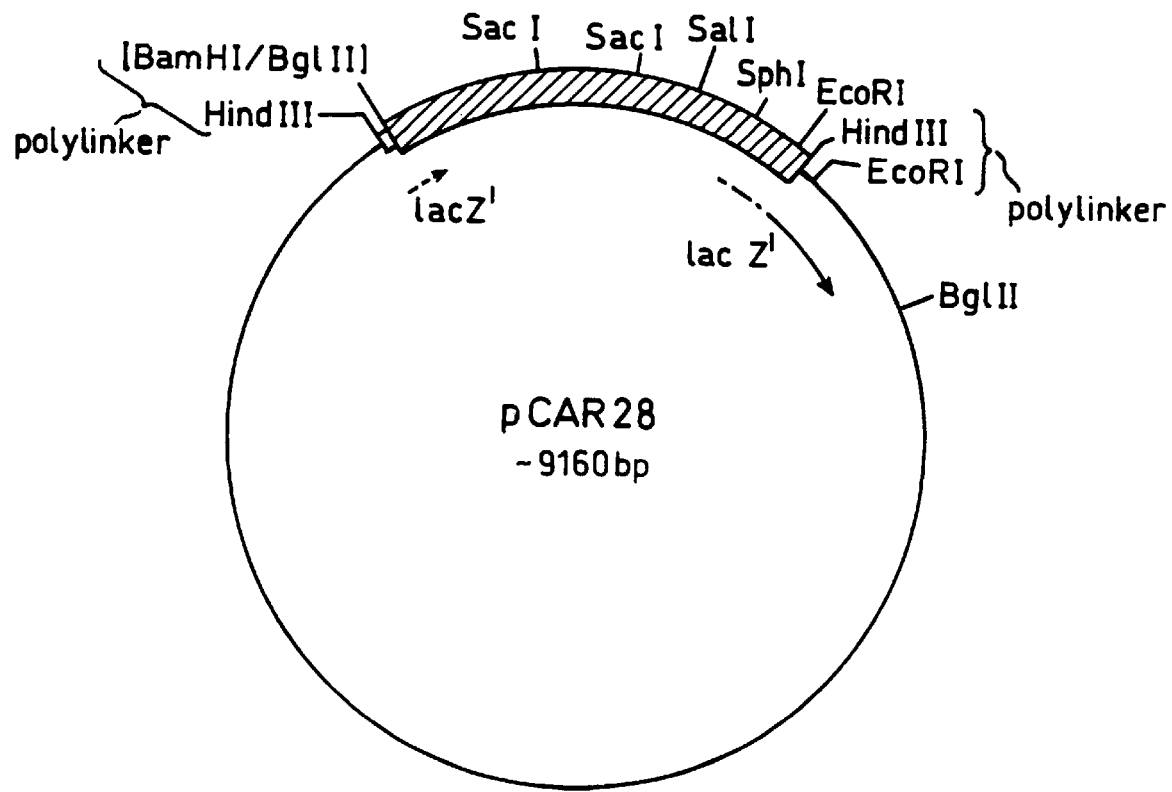
Figure 11:
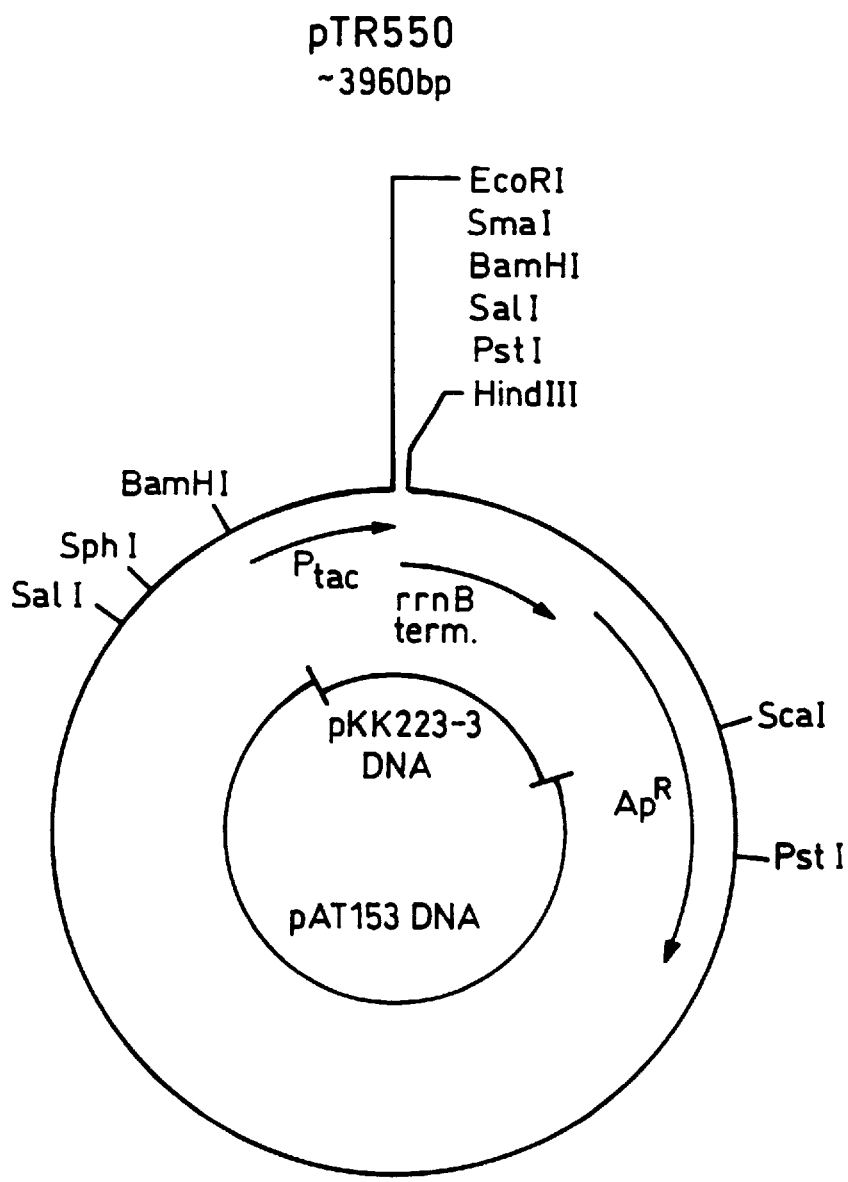
Figure 12:
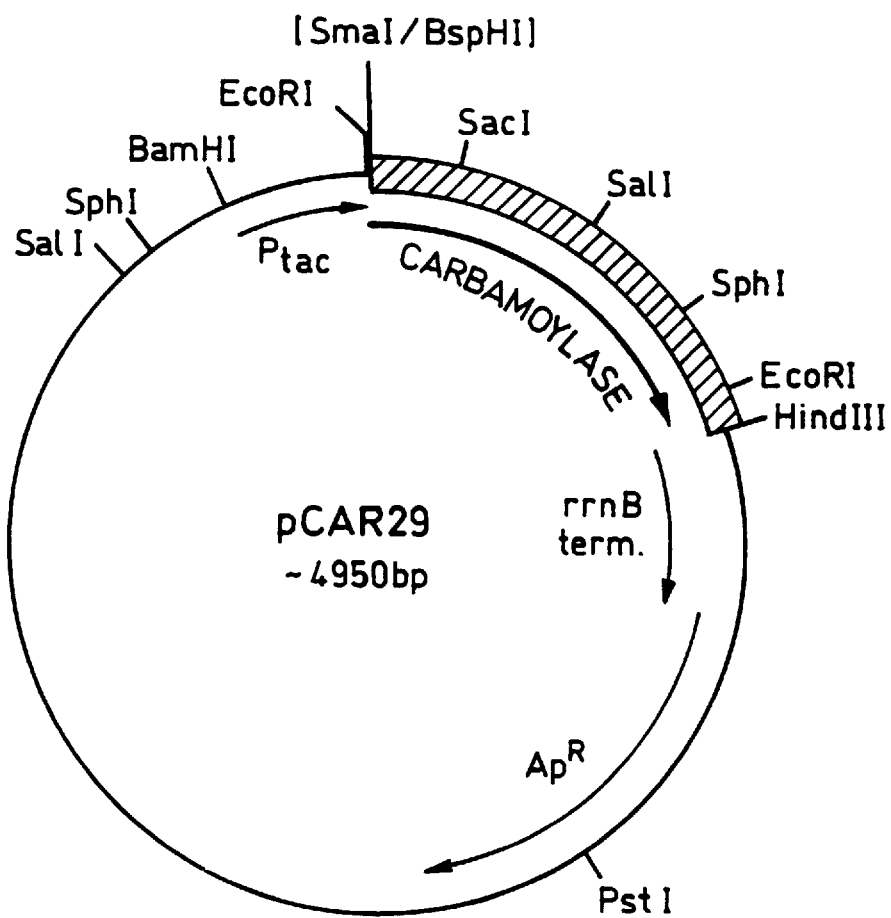

Abbn:

Non-shaded portion represents pCP19 DNA (cloned from pCAR12 together with Agrobacterium DNA), Shaded portion represents Agrobacterium DNA, Solid line represents pIJ2925 DNA FIG. 8 shows a restriction site and function map of plasmid pCAR27;

Abbn:

Solid line represents M13mp 19 DNA, Non-shaded portion represents pl J2925 DNA, Shaded portion represents Agrobacterium DNA FIG. 9 shows a restriction site and function map of plasmid pCAR28;

Abbn:

Solid line represents M13mp 19 DNA, Non-shaded portion represents pl J2925 DNA, Shaded portion represents Agrobacterium DNA FIGS. 10a and 10b show the sequence of the Agrobacterium DNA from pCAR27 and pCAR28. Only the "sense" or coding strand of the DNA molecule is shown. The DNA strand is shown 5'→3' from left to right. The nucleotide sequence is numbered immediately below the sequence. The amino acid sequence (using the three-letter code) of the carbamoylase encoded by the DNA is shown above each line of the nucleotide sequence;

FIG. 11 shows a restriction site and function map of pTR550;

Abbn:

rmB term. represents the transcriptional terminator from a ribosomal RNA operon, $^P$tac represents the tac promoter of transcription FIG. 12 shows a restriction site and function map of pCAR29;

Abbn:

Solid line represents pTR550 DNA, Shaded portion represents Agrobacterium DNA

Figure 13:
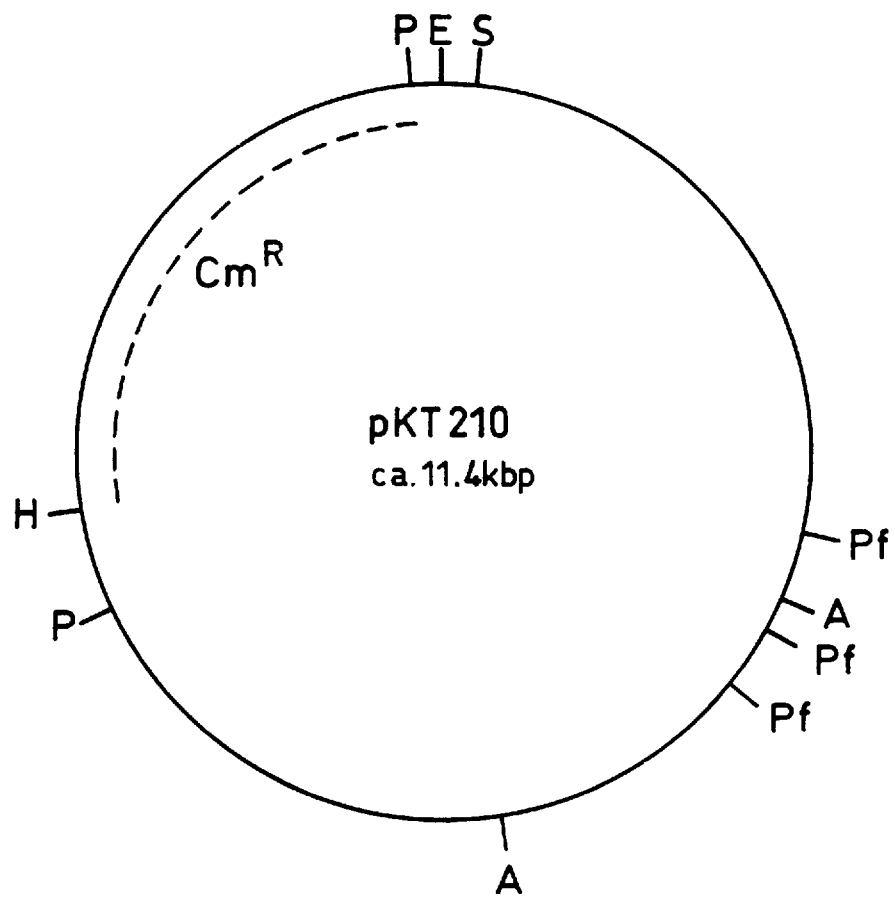

FIG. 13 shows a restriction site and function map of pKT210;

Abbn:

A=AccI, E=EcoRI, H=HindIII, Pf=PflMI, P=Pst I, S=Sal I

Figure 14:
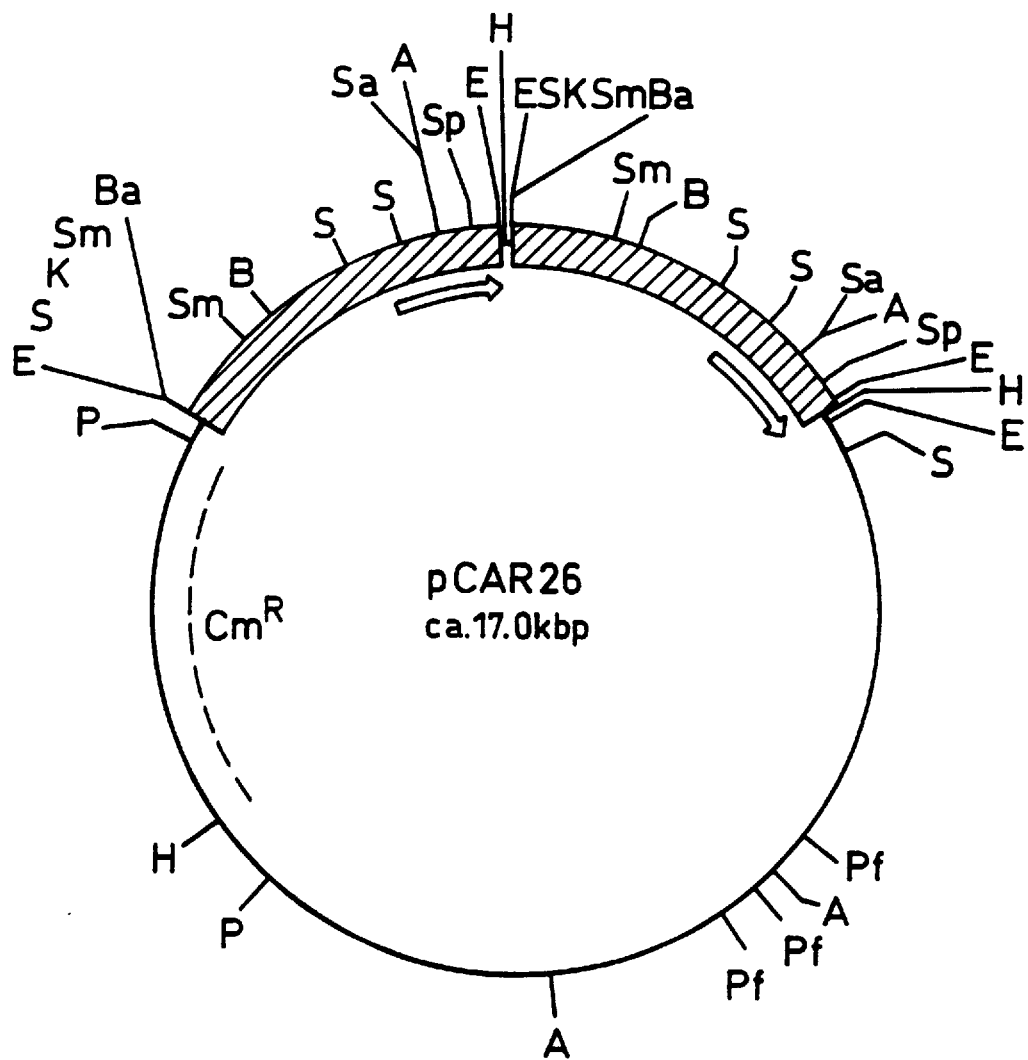
Figure 15:
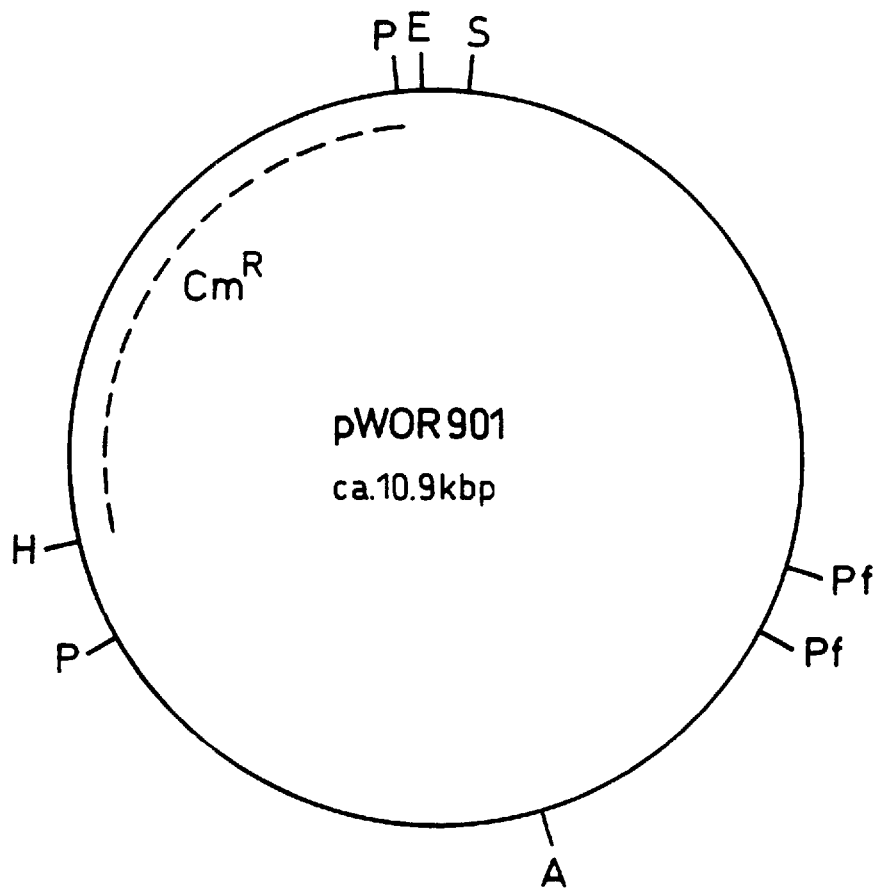

FIG. 14 shows a restriction site and function map of pCAR26;

Abbn:

A=AccI, B=Bgl II, Ba=BamHI, E=EcoRI, H=HindIII, P=Pst I, Pf=PflMI, S=Sst I, Sa=SalI, Sp=SphI, Sm=SmaI, K=KpnI, Shaded portion represents Agrobacterium DNA, Arrow represents carbamoylase coding sequence The vector DNA has not been mapped for all the enzymes that cut in the polylinker or Agrobacterium DNA. Not all of the Agrobacterium DNA has been mapped for AccI and PflMI FIG. 15 shows a restriction site and function map of pWOR901;

Abbn:

A=AccI, E=EcoRI, H=Hind III, Pf=PflMI, P=Pst I, S=Sst I

Figure 16:
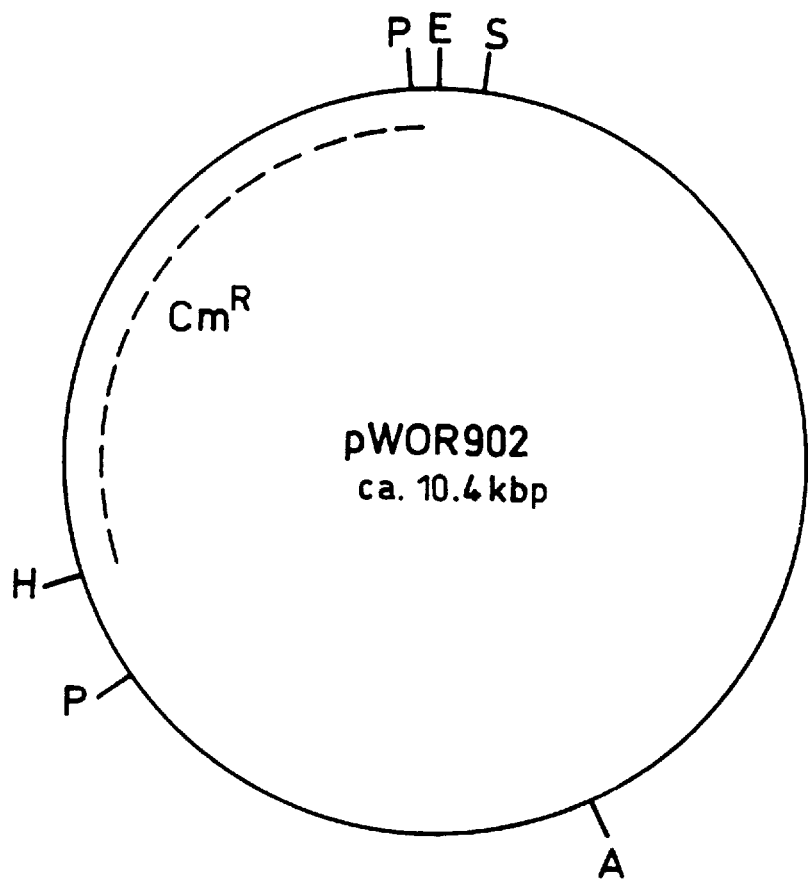
Figure 17:
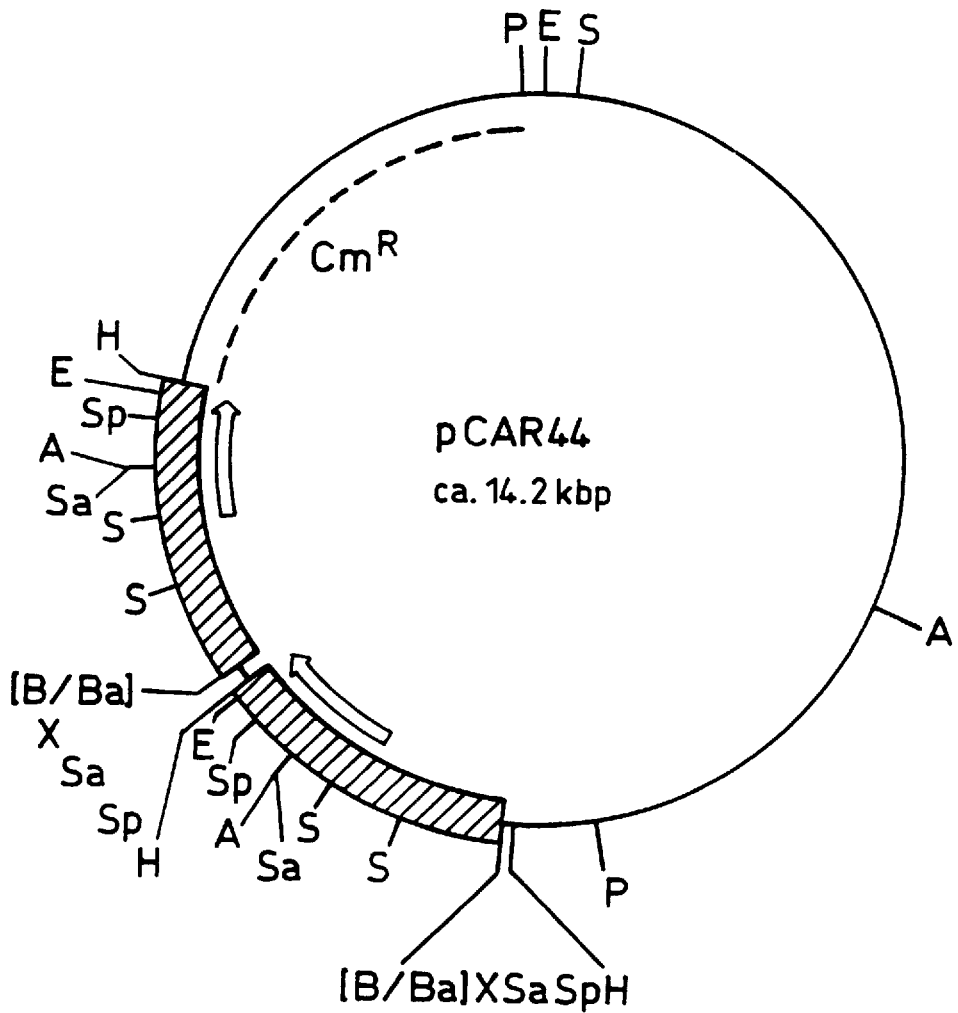

FIG. 16 shows a restriction site and function map of pWOR902;

Abbn:

A=AccI, E=EcoRI, H=Hind III, Pf=PflMI (no sites in pWOR902), P=Pst I, S=Sst I;

FIG. 17 shows a restriction site and function map of pCAR44;

Abbn:

A=AccI, B=Bgl II, Ba=Bam HI, E=EcoRI, H=Hind III, P=Pst I S=Sst I, Sa=SalI, Sp=SphI, X=XbaI, Shaded portion represents Agrobacterium DNA, Arrow represents carbamoylase coding sequence.

The vector DNA has not been mapped for all the enzymes that cut in the polylinker or Agrobacterium DNA.

Figure 18:
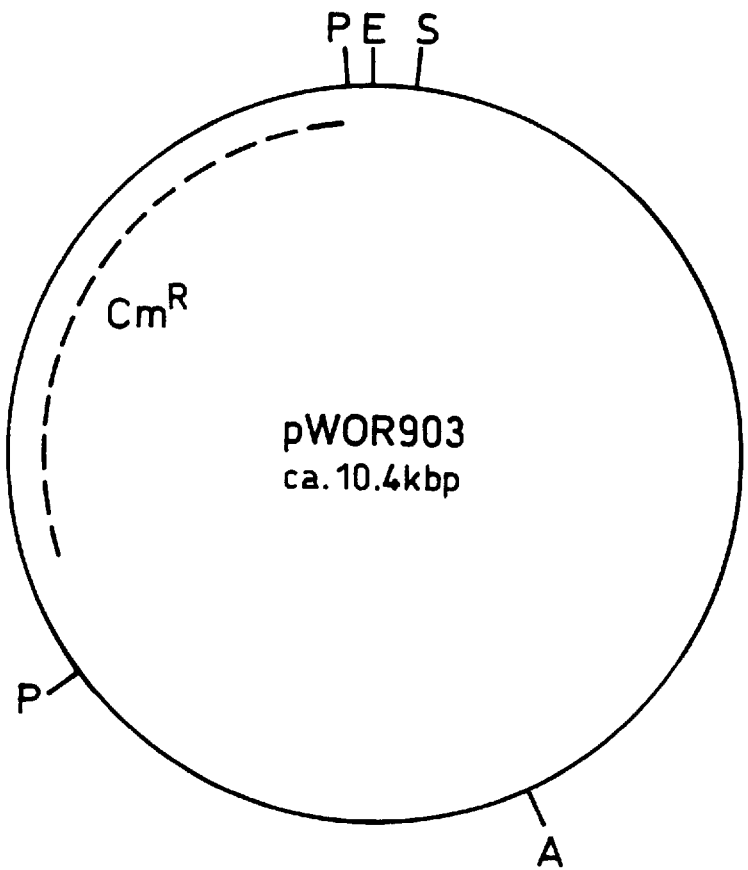

FIG. 18 shows a restriction site and function map of pWOR903;

Abbn:

A=AvaI, E=EcoRV, P=Pst I, S=Sst I

Figure 19:
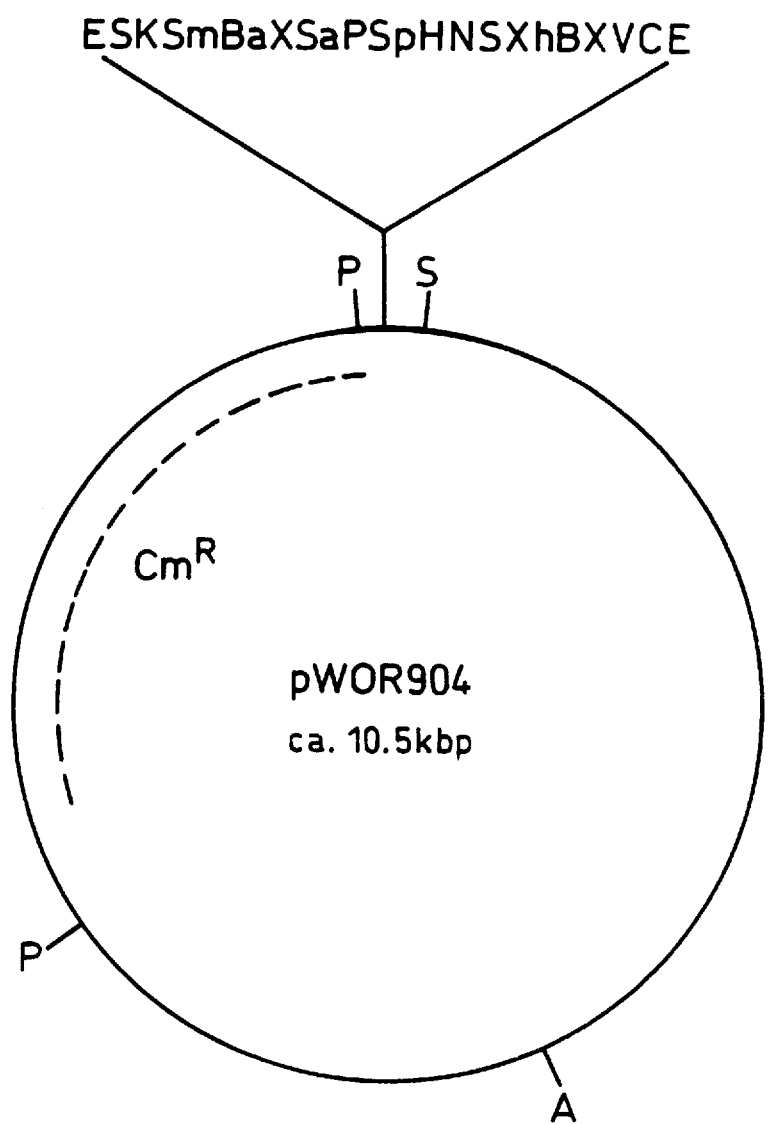

FIG. 19 shows a restriction site and function map of pWOR904;

Abbn:

A=AccI, B=Bal II, Ba=Bam HI, E=EcoRI, H=Hind III, P=Pst I, Sm=SmaI, S=Sst I, Sa=SalI, Sp=SphI, X=XbaI, V=EcoRV, C=CalI, K=KpnI, Xh=XhoI, N=NruI The vector DNA has not been mapped for all the enzymes that cut in the polylinker.

Figure 20:
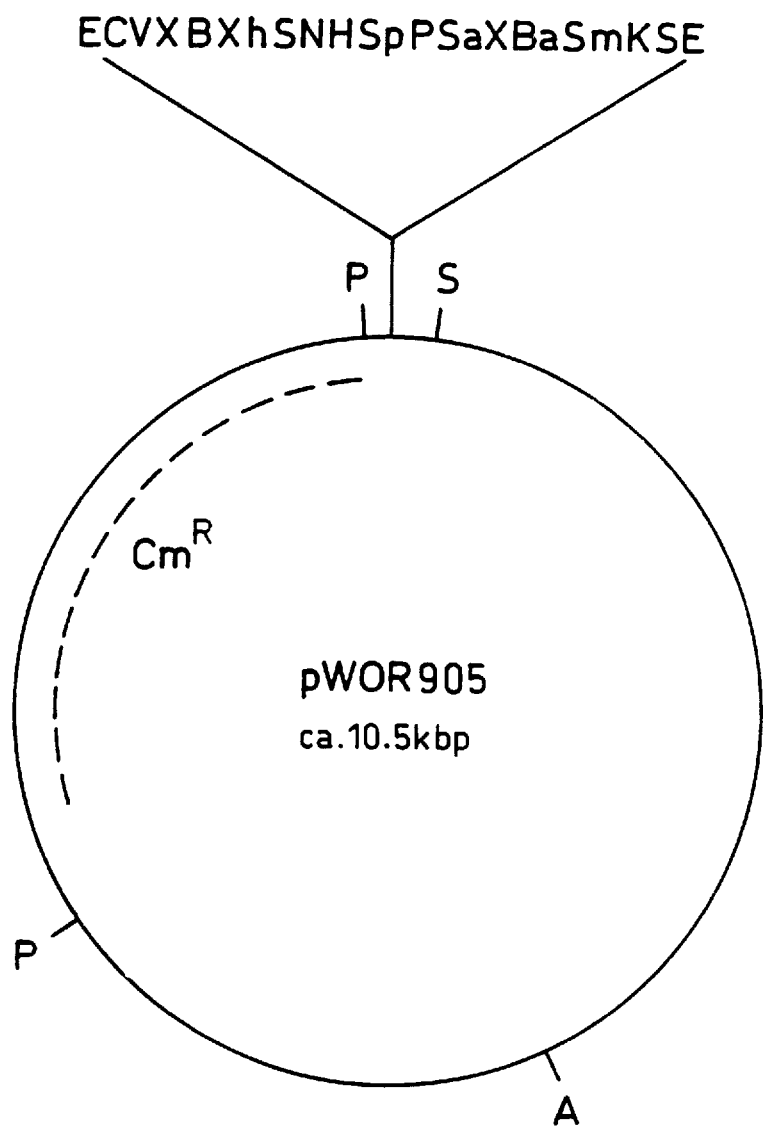

FIG. 20 shows a restriction site and function map of pWOR905;

Abbn:

A=AccI, B=Bal II, Ba=Bam HI, E=EcoRI, H=Hind III, P=Pst I, Sm=SmaI, S=Sst I, Sa=SalI, Sp=SphI, X=XbaI, V=EcoRV, C=CalI, K=KpnI, Xh=XhoI, N=NruI The vector DNA has not been mapped for all the enzymes that cut in the polylinker.

Figure 21:
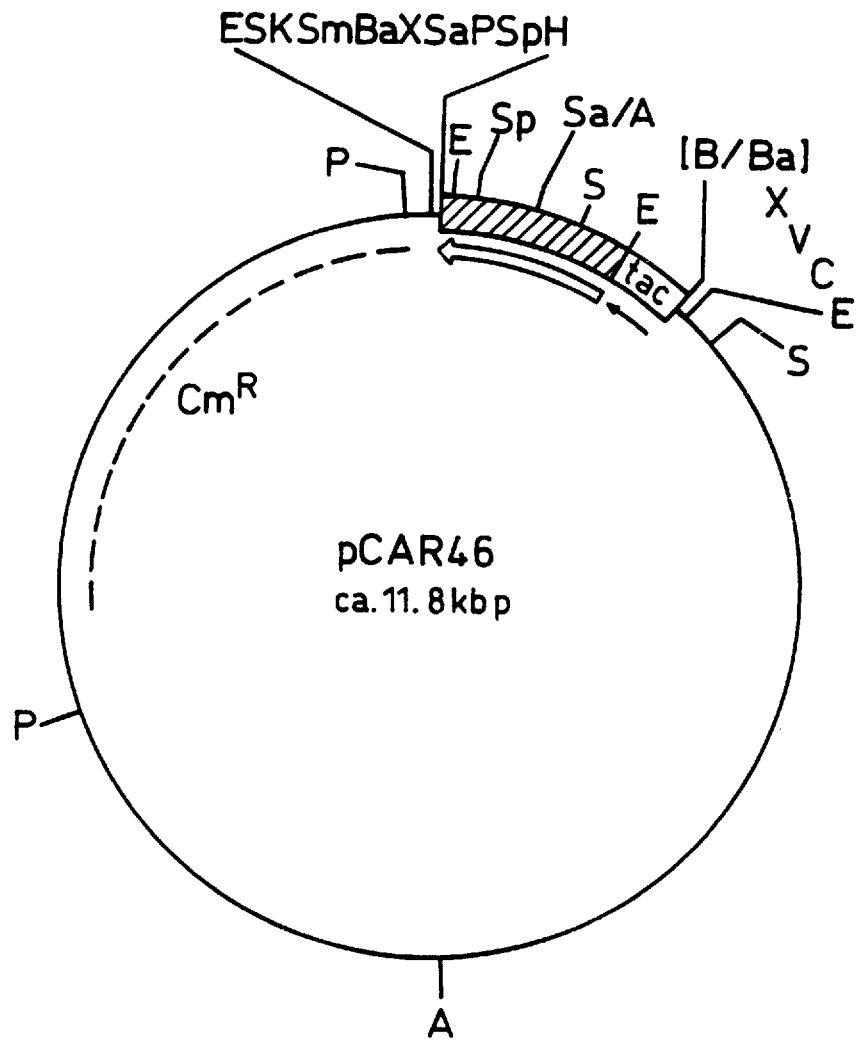
Figure 22:
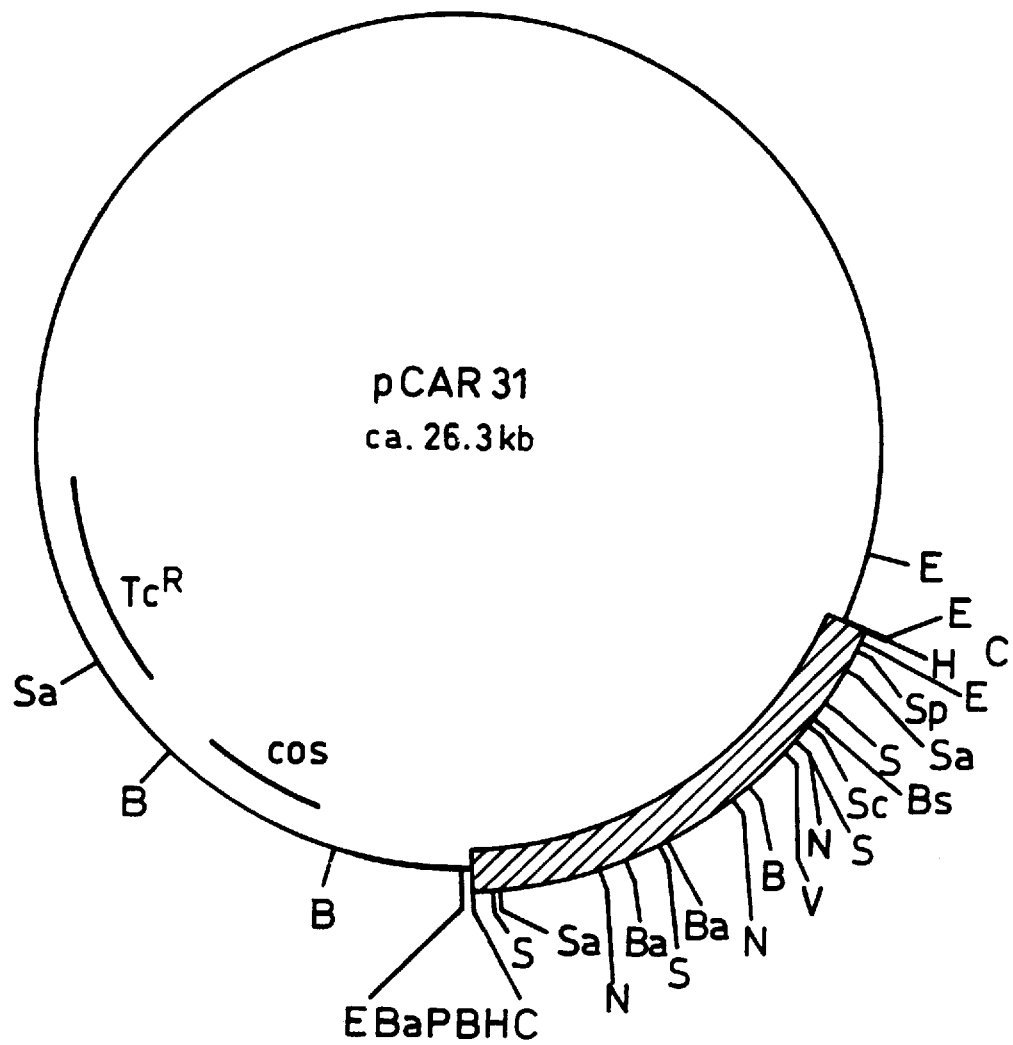
Figure 23:
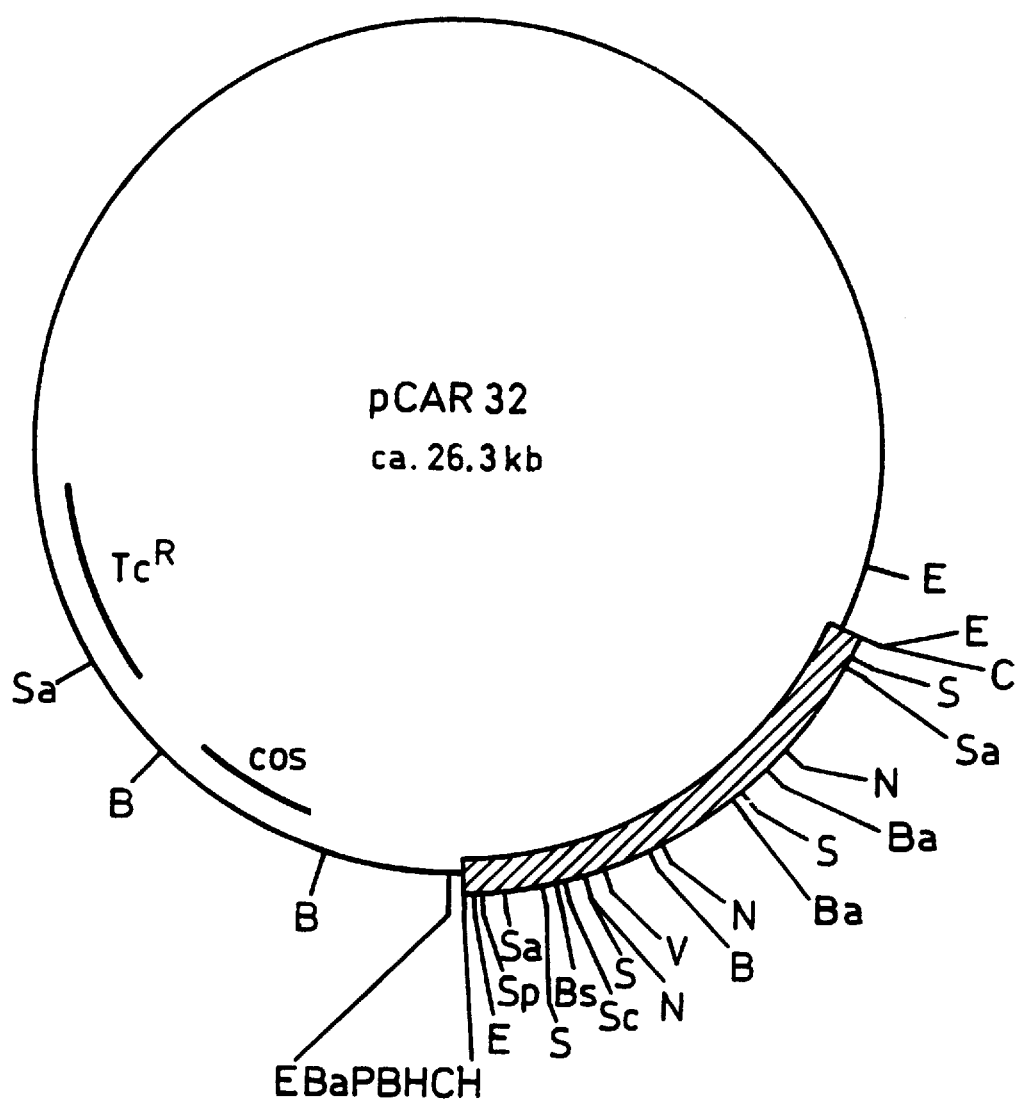
Figure 24:
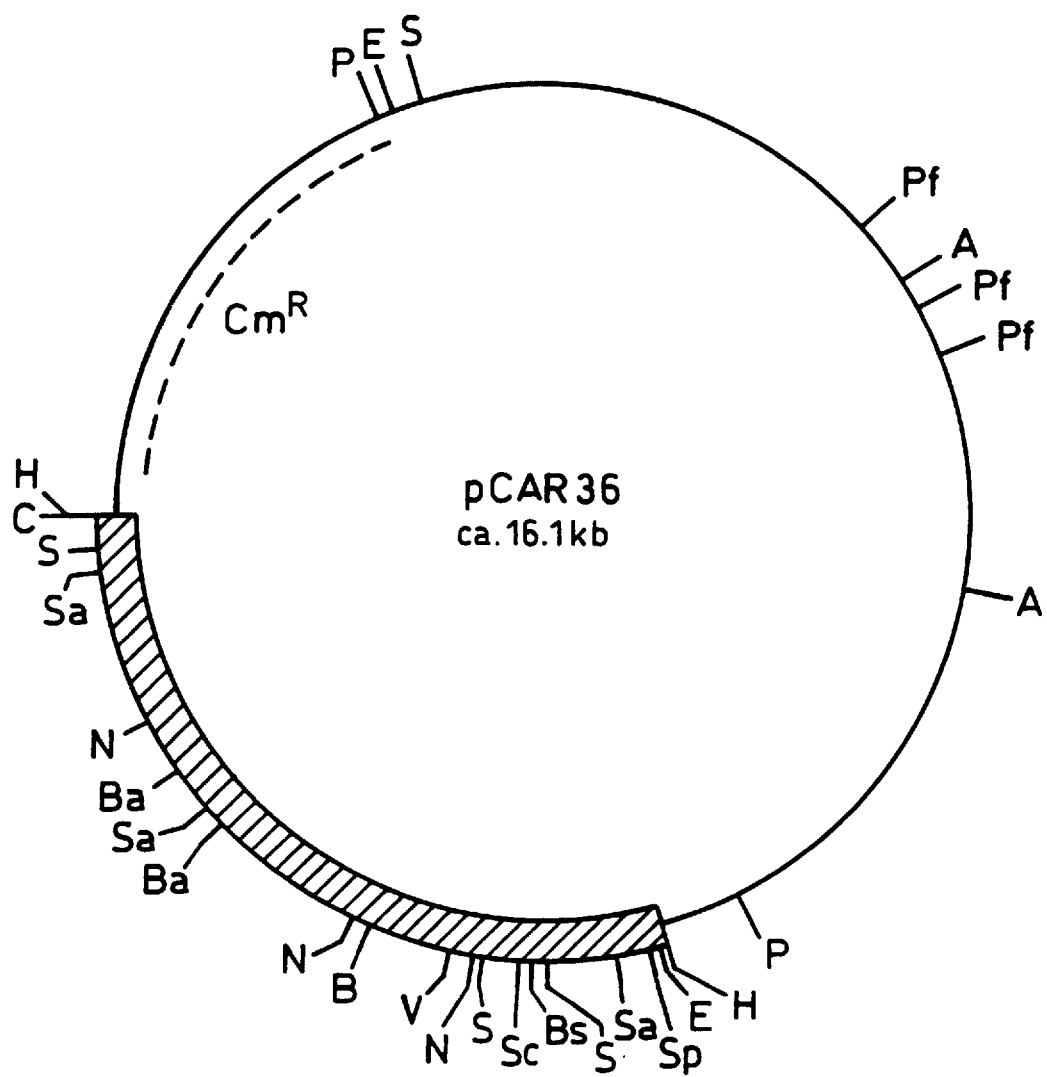
Figure 25:
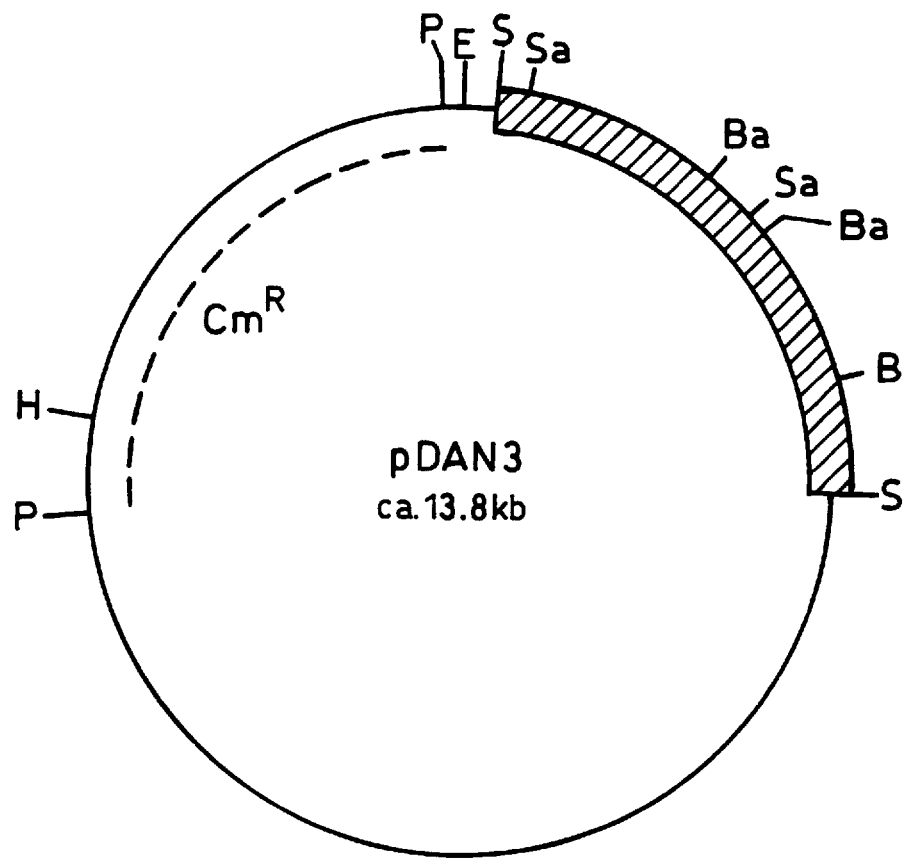
Figure 26:
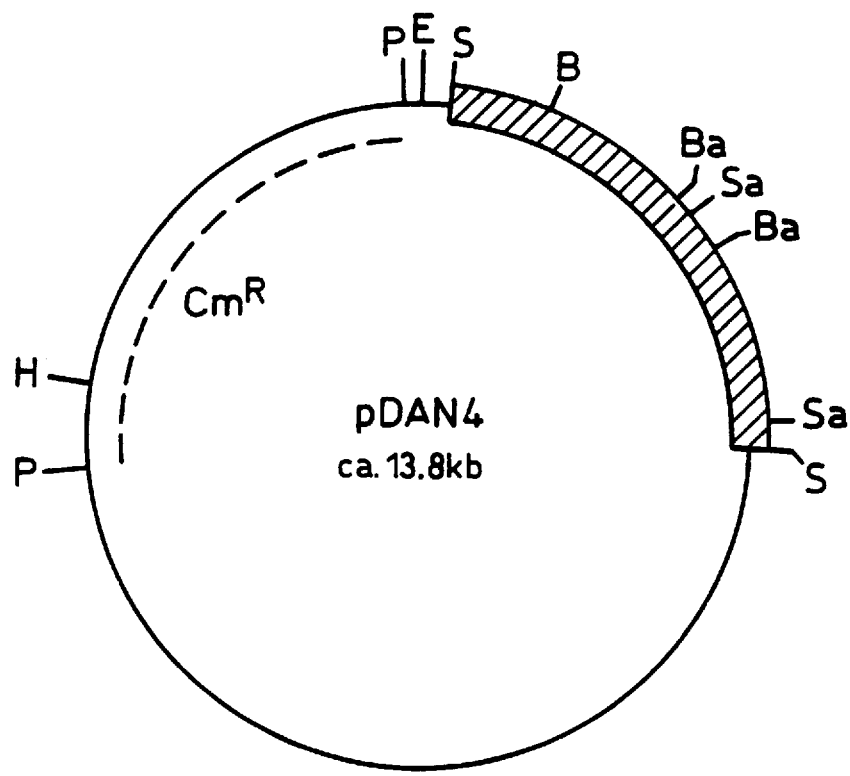

FIG. 21 shows a restriction site and function map of pCAR46;

Abbn:

A=AccI, B=Bal II, Ba=Bam HI, E=EcoRI, H=Hind III, P=Pst I, Sm=SmaI, S=Sst I, Sa=SalI, Sp=SphI, X=XbaI, V=EcoRV, C=CalI, K=KpnI, Shaded portion represents DNA from Agrobacterium 80/44-2A, Arrow represents carbamoylase coding sequence The vector DNA has not been mapped for all the enzymes that cut in the polylinker or Agrobacterium DNA;

FIG. 22 shows a restriction site and function map of pCAR31;

Abbn:

B=Bgl II, Ba=Bam HI, Bs=BspHI, C=ClaI, E=EcoRI, V=EcoRV, H=Hind III, N=NruI, P=Pst I, S=SstI, Sa=SalI, Sp=SphI, Sc=ScaI, $Tc^R$=Tetracycline resistance gene, cos=cos site from bacteriophage λ, Shaded portion represents Agrobacterium DNA FIG. 23 shows a restriction site and function map of pCAR32;

Abbn:

B=Bgl II, Ba=Bam HI, Bs=BspHI, C=ClaI, E=EcoRI, V=EcoRV, H=Hind III, N=NruI,P=Pst I, S=SstI, Sa=SalI, Sp=SphI, Sc=ScaI, $Tc^R$=Tetracycline resistance gene, cos=cos site from bacteriophage λ, Shaded portion represents Agrobacterium DNA FIG. 24 shows a restriction site and function map of pCAR36;

Abbn:

A=AccI, B=Bgl II, Ba=Bam HI, Bs=BspHI, C=ClaI, E=EcoRI, V=EcoRV, H=Hind III, N=NruI, P=Pst I, Pf=PflMI, S=SstI, Sa=SalI, Sp=SphI, Sc=ScaI, $Cm^R$=chloramphenicol resistance gene, Shaded portion represents Agrobacterium DNA FIG. 25 shows a restriction site and function map of pDAN3;and Abbn:

B=Bgl II, Ba=Bam HI, E=EcoRI, H=Hind III, P=Pst I, S=SstI, Sa=SalI, Sp=SphI, X=XbaI, Shaded portion represents Agrobacterium DNA FIG. 26 shows a restriction site and function map of pDAN4.

Abbn:

B=Bgl II, Ba=Bam HI, E=EcoRI, H=Hind III, P=Pst I, S=SstI, Sa=SalI, Sp=SphI, X=XbaI, Shaded portion represents Agrobacterium DNA The DNA of the invention may be ligated to any suitable vector.

Normally the vector is a plasmid, for example a plasmid derived from *E. coli,* or is a temperate or virulent bacteriophage.

Particular vectors include broad host range vectors such as pCP19 or pKT210 or derivatives thereof. The vectors pIJ2925 and pTR550, described in detail herein, may also advantageously be used.

A particularly useful vector is the mobilisation defective (Mob⁻) vector pWOR902, a derivative of pKT210. pWOR902, obtained by a spontaneous deletion of DNA from the Mob⁻ unstable vector pWOR901, is less promiscuous than pKT210. An advantage of pWOR902 is thus that recombinant strains are safer when transformed by pWOR902 than, for example, pKT210. *E. coli* HB 101 (pWOR902) was deposited at the National Collection of Industrial and Marine Bacteria, Aberdeen, Scotland on 4th Nov. 1991 under the accession number NCIMB 40451. The deposit was made under the Budapest Treaty on the deposition of micro-organisms for the purposes of patent procedure. pWOR902, derivatives thereof and hosts transformed thereby form a further aspect of this invention.

Particularly useful derivatives of pWOR902 are the plasmids pWOR903, pWOR904 and pWOR905 described hereinbelow. These may be obtained from pWOR902 by standard methodology.

The recombinant vector according to the invention may be prepared by standard techniques, for example by ligating DNA comprising the carbamoylase gene to the chosen vector via direct combination of cohesive ends, homopolymer tailing or by means of a linker or adapter molecule.

It will be appreciated that recombinant vectors prepared according to the above methods may contain the insert DNA in one of two possible orientations. Recombinant vectors having the insert DNA in each orientation are included within the scope of the invention.

Particular recombinant vectors include those designated as pCAR 1, pCAR6, pCAR12, pCAR21, pCAR26, pCAR27, pCAR28, pCAR29, pGal2789RS3Carb, pCAR31, pCAR32, pCAR36, pCAR44 and pCAR46, the preparation and characterisation of which are described in detail hereinbelow.

In a particularly preferred aspect of the invention, plasmids pCAR26, pCAR44 and pCAR46 are provided. pCAR26, and especially, pCAR44 and pCAR46 give a large amount of carbamoylase activity when host cells, especially Agrobacterium, are transformed thereby and are cultured under suitable conditions.

It will be appreciated that the carbamoylase protein coding sequence may be expressed from a heterologous promoter such as the tac promoter. Such expression is included within the scope of the invention.

In a specific aspect the invention provides a host, especially Agrobacterium, transformed with pCAR46. In a specific aspect the invention provides NCIMB 40478 deposited under the Budapest Treaty on 14th Feb. 1992.

A process for obtaining DNA encoding the carbamoylase enzyme comprises the steps of:

a) constructing a gene library from chromosomal DNA fragments obtained from a carbamoylase producing micro-organism;

b) carrying out one or more hybridisation experiments in order to select from the said library clones which contain the DNA of the invention; and c) isolating the DNA of the invention.

The gene library may be prepared by conventional 'shotgun' methodology by:

(a) partial digestion of the chromosomal DNA of a carbamoylase producing micro-organism with one or more suitable restriction endonucleases, for example HindIII;

(b) size fractionation to give fragments of appropriate length;

(c) ligation of the fragments into a vector to obtain a recombinant vector; and (d) transformation or transfection of a suitable host with the recombinant vector.

As described herein, transformation or transfection may be carried out by conventional methods well known in the art.

Size fractionation may suitably be carried out on a sucrose gradient and fragments within chosen size limits may be selected.

In a preferred aspect a 'gene library' may be prepared by selecting fragments of about 15 to 30 kb, in length and ligating the said fragments into a plasmid vector, for example the vector pCP19. A suitable host is *E. coli*, for example *E. coli* DH1.

In order to identify clones in the gene library which contain the carbamoylase gene, it is necessary to screen colonies for the ability to convert N-carbamoyl-4-hydroxyphenylglycine into D(−)4-hydroxy phenylglycine. 'Positive' colonies may conveniently be identified and isolated by testing for the production of ammonia (formed in the above reaction) by standard methods, for example by use of an indicator such as phenol red.

To enable the skilled person readily to perform the invention a colony which was positive in this test, specifically an *E. coli* AG1 micro-organism transformed with pCAR1, was deposited at the National Collection of Industrial and Marine Bacteria, Aberdeen, Scotland on 26th Apr., 1989 under the Accession Number NCIMB 40133. *E. coli* NCIMB 40133 forms a further aspect of the present invention.

The plasmid DNA present in a positive colony, for example *E. coli* NCIMB 40133, may be further manipulated as described in the Examples herein to allow determination of the sequence of the carbamoylase enzyme encoded thereby [see FIG. 10(*b*) below].

It will be understood that the amino acid sequence of this naturally occurring enzyme may be subject to some variability. These have substantially the same amino acid sequence as shown in FIG. 10(*b*) below and have carbamoylase activity.

In a specific embodiment of the invention there is provided DNA or recombinant DNA comprising the coding sequence from nucleotide 891 to nucleotide 1802 shown in FIG. 10(*b*) SEQ ID NO:1 below. The DNA sequence encodes a carbamoylase enzyme with a calculated molecular weight of approximately 34,100.

In a further aspect of the invention there is provided a substantially purified carbamoylase enzyme having the amino acid sequence from N- to C-terminus shown in FIG. 10(*b*) SEQ ID NO:2.

In yet a further aspect of this invention there is provided a carbamoylase enzyme as described hereinabove immobilised on a solid support, for example an anion exchange resin such as the phenol-formaldehyde anion exchange resin Duolite A568 (Rohm and Haas).

The DNA coding sequence or amino acid sequence shown in FIG. 10(*b*) can, if desired, be synthesized by conventional means, for example using an automated synthesiser.

Owing to the degenerate nature of the genetic code the amino acid sequence of the carbamoylase enzyme can be encoded by numerous alternative DNA sequences.

It will be understood that the DNA of the present invention further comprises such alternative sequences.

In yet another aspect the invention provides a DNA compound selected from:

a) a portion of the DNA insert of pCAR1, said portion being a BspHI-HindIII fragment of 986 base pairs;

b) DNA sequences which hybridise to the said portion under stringent conditions and which code for a carbamoylase enzyme capable of converting a D-N-carbamoyl (optionally substituted phenyl)glycine into the corresponding D-(optionally substituted phenyl)glycine.

In a particular aspect of the invention it has been found that the carbamoylase enzyme may be conveniently produced in *E. coli* despite initial difficulties in getting generation of soluble active enzyme using standard methods. In this aspect of the invention DNA comprising the carbamoylase gene is first cloned into any suitable vector which is, or has been, manipulated so that the gene is expressed in *E. coli* under the control of a suitable promoter.

Preferably the vector is a high copy number plasmid, for example pUC 18 or a derivative of the naturally occurring *E. coli* plasmid NR1 (Foster, T. J. et al, *J. Bact*, 1975, 124, 1153).

To achieve effective expression of carbamoylase enzyme the promoter is preferably non-inducible, i.e. there is no requirement to add chemicals or increase temperature to derepress or induce it. Surprisingly, it has been found that, under these conditions, *E. coli* cells produce, throughout their growth cycle, carbamoylase enzyme which is both soluble and active.

One preferred promoter for expression of the carbamoylase enzyme in *E. coli* is the galactose promoter as described hereinbelow.

Plasmid DNA present in *E. coli* NCIMB 40133 or derivatives thereof may also be manipulated to give high level expression of hydantoinase as herein described.

The following examples illustrate the invention.

EXAMPLE 1

Culture of Agrobacterium 80/44-2A and Isolation of Chromosomal DNA 50 ml of AJ-1 broth (20 g yeast extract, 1 g $KH_2PO_4$, 1 g $K_2HPO_4$, 0.5 g $MgSO_4.7H_2O$, 0.1 g $CaCl_2.2H_2O$, 15 mg $MnSO_4.4H_2O$, 20 mg $FeSO_4.7H_2O$ and 5 g glucose per liter, adjusted to pH 7.0 with 5M NaOH) was inoculated with a culture of Agrobacterium 80/44-2A, (isolated from soil) and incubated in a gyrotory incubator at 25° C. for about 24 hours. The culture was centrifuged at approximately 1500 x g for 7 minutes at 10° C. The resulting supernatant was discarded, and the cell pellet was washed in 10 ml of saline phosphate buffer (8.5 g NaCl, 7.2 g $K_2HPO_4$, 7.0 g $K_2HPO_4$ per liter) and then repelleted. The supernatant was discarded and the cell pellet was resuspended in 8 ml of a lysing solution of 3% SDS (sodium dodecyl sulphate) and 50 mM Tris-HCl, pH 8.0, and incubated in a water bath at 65° C. for 15 minutes. The solution of lysed cells was allowed to cool to room temperature and was extracted twice with 5 ml of buffered phenol/chloroform (a 50:50 mixture of phenol and chloroform buffered to a pH of approximately 7 with Tris-HCl, pH 8.0). The recovered aqueous phase was extracted with 5 ml of chloroform. The recovered aqueous phase was precipitated by adding 0.1 volume of 3M sodium acetate (NaOAc), mixing, layering 2.5 volumes of cold (−20° C.) ethanol onto the solution and swirling to mix. The clot of precipitated DNA was spooled onto a glass rod and redissolved in 3 ml of TE (10 mM Tris-HCl, pH 8.0; 1 mM EDTA, pH=8.0) containing 40 µg/ml Ribonuclease A. The solution was incubated at 37° C. for 30 minutes, extracted with buffered phenol/chloroform, extracted with chloroform, and then precipitated with NaOAc and ethanol. The DNA was spooled onto a glass rod and redissolved in 3 ml of TE.

EXAMPLE 2

Construction of Genomic Library of Agrobacterium 80/44-2A

Figure 1:
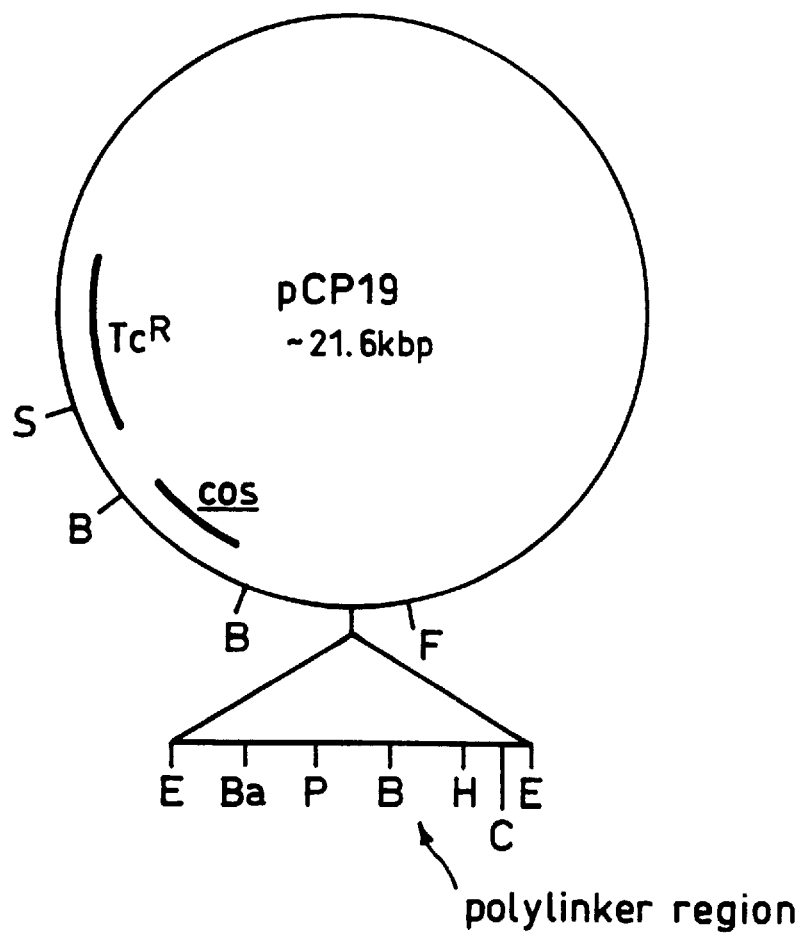

The plasmid vector pCP19 (FIG. 1) is a derivative of the broad host range plasmid pLAFR1 (Friedman et al., Gene 18 (1982) 289–296) and is similar to pCP13 (described by Darzins and Chakrabarty, Journal of Bacteriology 159 (1984) 9–18) but lacks the kanamycin resistance gene present in pCP13. 2 µg of plasmid pCP19 were digested with 20 units of restriction enzyme Hind III (Gibco BRL, Paisley, PA3 4EF, Scotland) at 37° C. for 3 hours in Hind III digestion buffer (50 mM Tris-HCl, pH 8.0; 10 mM $MgCl_2$; 100 mM NaCl). The mixture was extracted with buffered phenol/chloroform, then extracted with chloroform and the recovered aqueous phase was treated with 0.1 volume 3M NaOAc and 2.5 volumes ethanol. The mixture was incubated at −20° C. for 1 hour to precipitate the DNA. After centrifugation in microcentrifuge tubes at 12000 x g for 5 minutes, the DNA pellet was redissolved in 50 μl of 50 mM Tris-HCl (pH 8.0), 0.1 mM EDTA (pH 8.0). One unit of calf intestinal alkaline phosphatase (CIAP; from BCL, Boehringer Mannheim House, Lewes, East Sussex, BN7 1LG) was added and the mixture was incubated at 37° C. for 30 minutes. 45 μl of water and 5 μl of a 10% solution of SDS were added and the mixture was incubated at about 68° C. for 15 minutes. The mixture was then cooled to room temperature, extracted with buffered phenol/chloroform, extracted with chloroform and precipitated by adding NaOAc and ethanol. The DNA pellet was redissolved in 40 μl of TE.

25 μg of DNA from Agrobacterium 80/44-2A (Example 1) were digested with 12 units of Hind III in 150 μl of Hind III digestion buffer (50 mM Tris-HCl, pH 8.0; 10 mM $MgCl_2$; 100 mM NaCl) at 37° C. for 10 to 30 minutes to obtain cleavage at some, but not all, of the recognition sites for the restriction enzyme. The progress of the digestion was monitored by removing aliquots and stopping the reaction by phenol/chloroform extraction. Portions of the DNA samples recovered were fractionated by electrophoresis on a 0.6% agarose (Ultrapure, from Gibco BRL) gel in TBE buffer (89 mM Tris base; 89 mM boric acid; 2 mM EDTA, pH 8.0) containing 0.5 μg/ml ethidium bromide, and the DNA bands were visualized using ultraviolet light. The required sizes of partially digested DNA fragments are approximately 15 to approximately 30 kbp. These fragments were obtained by choosing suitable aliquots from the partial digestion, combining them, and fractionating them by electrophoresis on a 0.8% low melting point agarose (Ultrapure, from Gibco BRL) gel in TBE buffer containing ethidium bromide. After visualizing the DNA bands with ultraviolet light, the portion of the gel corresponding to fragments of size ca. 15 kbp to ca. 30 kbp was cut out and melted at 65° C. for 15 minutes. The mixture was cooled to about 37° C., and extracted twice with a solution of phenol buffered to neutral pH with Tris-HCl (pH 8.0). The recovered aqueous phase was extracted with buffered phenol/chloroform, extracted with chloroform and the DNA was precipitated by adding NaOAc and ethanol. The DNA was redissolved in 100 μl of TE.

About 0.8 μg of Hind III-digested, CIAP-treated pCP19 DNA, and about 4 μg of Hind III partially digested chromosomal DNA of Agrobacterium 80/44-2A were co-precipitated by adding NaOAc and ethanol, and were redissolved in 12 μl of DNA ligase buffer (30 mM Tris-HCl, pH 8.0; 4 mM $MgCl_2$; 10 mM dithiothreitol; 50 μg/ml bovine serum albumin, and 0.5 mM ATP). One unit of T4 DNA ligase (Gibco BRL) was added and the mixture was incubated at 12° C. for about 16 hours. 3 μl of the ligated DNA was packaged into lambda bacteriophage particles using the Gigapack Gold Packaging Kit from Stratagene, La Jolla, Calif. 92037 (see also Enquist and Sternberg, Methods in Enzymology 68 (1979) 281–298). This gave 500 μl of a suspension of bacteriophage particles.

A 10 ml culture of *Escherichia coli* AG1 (a derivative of *E. coli* DH1:Hanahan, Journal of Molecular Biology 166 (1983) 557–580), obtained from Stratagene, was grown in L-broth (10 g bacto-tryptone, 5 g yeast extract, 5 g NaCl and 1 g glucose per liter), containing 0.4% maltose and 10 mM $MgSO_4$, at 37° C. on a gyrotory incubator for approximately 16 hours. The cells were collected by centrifugation at ca. 1500 x g for 7 minutes and resuspended in 10 mM $MgSO_4$ to a final optical density at 600 nm of 0.5. Eleven aliquots of 400 μl of cells of the *E. coli* culture were each mixed with 40 μl of bacteriophage particles and incubated at 37° C. for 15 minutes. Each mixture was added to 800 μl of L-broth, incubated on a shaker at 37° C. for 1 hour and centrifuged at 12000 x g for 2 minutes to pellet the cells. Each cell pellet was resuspended in 100 μl of L-broth and spread on one L-agar (as for L-broth but containing 1.5% agar) plate supplemented with 10 μg/ml tetracycline. The plates were incubated at 37° C. for about 16 hours. 800 colonies were picked off to L-agar plates containing tetracycline (10 μg/ml) such that each plate had 50 colonies. These plates were incubated at 37° C. for about 16 hours, and then each plate was replica-plated to 2 L-agar plates, containing tetracycline, which were incubated at 37° C. for about 16 hours. Two sets of 16 plates resulted; these sets were copies of a Genomic Library of Agrobacterium 80/44-2A DNA in *E. coli*.

EXAMPLE 3

Isolation of a Clone Specifying Carbamoylase Activity

Figure 2:
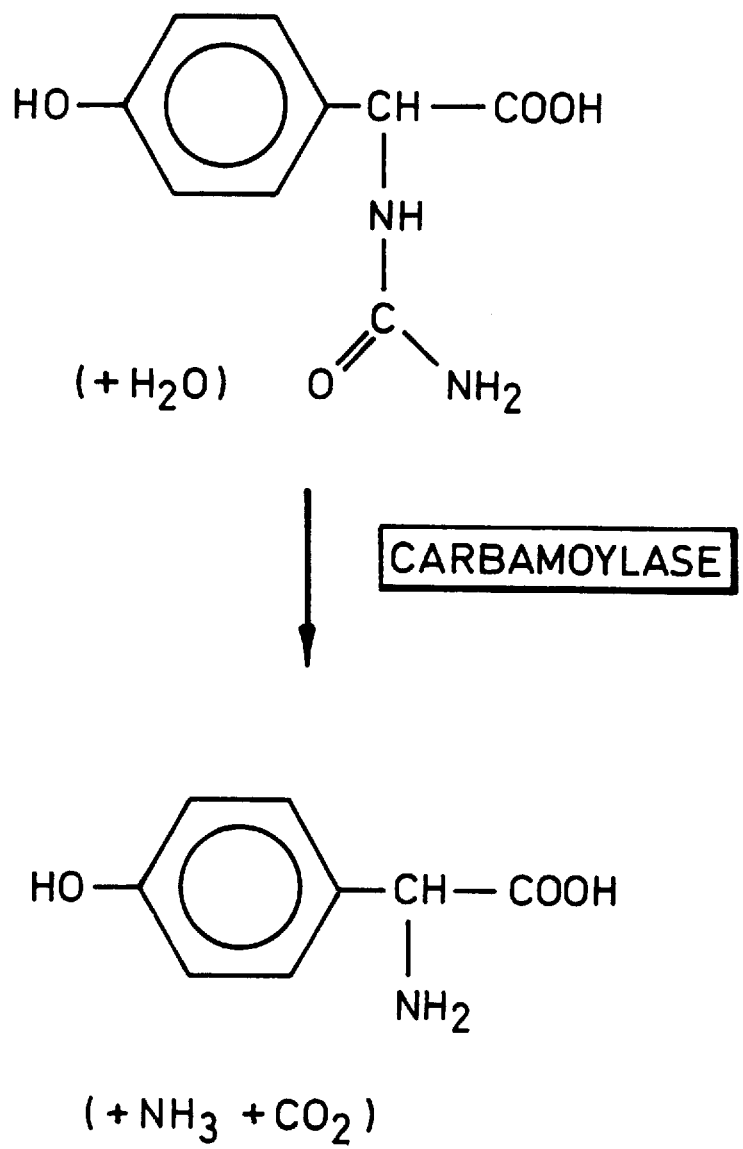
FIG. 2 shows the reaction sequence for conversion of N-carbamoyl-p-hydroxyphenylglycine to D(-)p-hydroxyphenylglycine.

One set of 800 colonies (Example 2), representing a Genomic Library of Agrobacterium 80/44-2A DNA in the plasmid pCP19 in *E. coli* AG1, was screened for the ability to convert N-carbamoyl-p-hydroxyphenylglycine (N-carb.) to D(−)p-hydroxyphenylglycine (D(−)HPG). Cells from half of one plate (i.e. from 25 different clones) of the library were scraped off into a microcentrifuge tube containing 800 μl of assay buffer. The assay buffer was a solution of 1% N-carb., 10 mM phosphate buffer, 0.0012% phenol red (0.6 ml of a 2% solution per 100 ml of N-carb. solution) adjusted to pH 6.7 with NaOH. This solution was a yellowish colour. The contents of the tube were mixed, and the tube was incubated in a water bath at 42° C. for 24 hours. Conversion of N-carb. to D(−)HPG results in production of ammonia (FIG. 2) which raises the pH and can be detected by a change in the colour of the phenol red from yellow to pinkish-red. One of the 32 tubes changed colour to pinkish-red. The 25 colonies corresponding to this tube were restreaked, from the relevant plate of the duplicate library, onto L-agar plates containing tetracycline, which were incubated at 37° C. for about 16 hours. A loopful of cells from each restreak was tested for carbamoylase activity using the phenol red test described above. One of the 25 colonies produced a pinkish-red colour. The reaction tube was centrifuged at 12000 x g for 2 minutes to pellet the cells and the supernatant was assayed by HPLC to confirm that D(−)HPG was present. The clone encoding carbamoylase activity was deposited at the National Collection of Industrial and Marine Bacteria, Aberdeen, Scotland on 26th Apr., 1989 under the accession number NCIMB 40133. The deposit was made under the Budapest Treaty on the deposition of micro-organisms for the purposes of patent procedure.

EXAMPLE 4

Isolation and Characterization of pCAR1 from *Escherichia coli* NCIMB 40133

Figure 3:
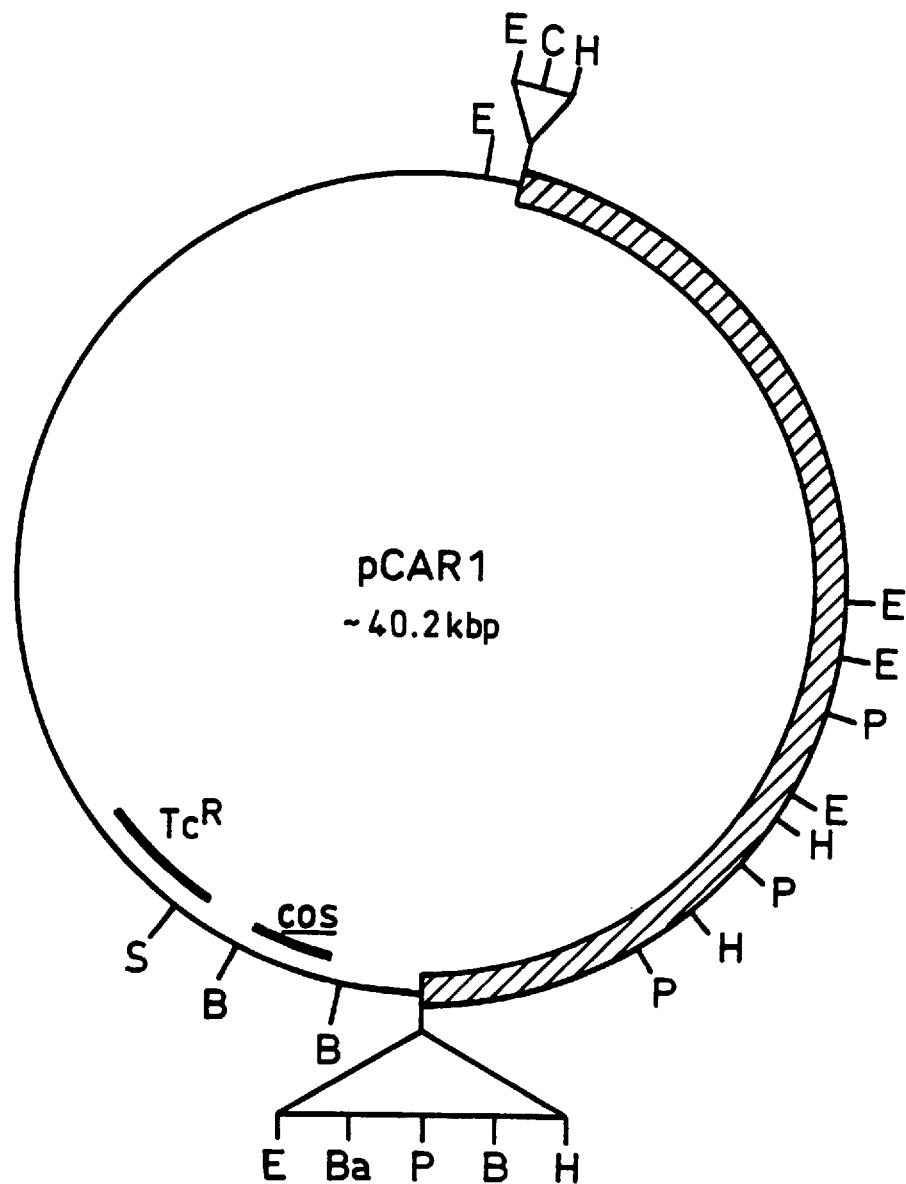
FIG. 3 shows a restriction site and function map of plasmid pCAR 1.

400 ml of L-broth containing 10 μg/ml tetracycline was inoculated with a culture of *E. coli* NCIMB 40133 (Example 3) and incubated in a gyrotory incubator at 37° C. for about 20 hours. The culture was centrifuged at ca. 6000 x g for 10 minutes at 4° C., and the resulting cell pellet was resuspended in 2.5 ml of 25% sucrose, 50 mM Tris-HCl (pH 8.0). 0.5 ml of a 10 mg/ml lysozyme solution was added and the mixture was incubated on ice for 10 minutes. 1 ml of 0.25M EDTA (pH 8.0) was added to the lysozyme-treated cells, followed by 4 ml of lysing solution (0.25% Triton X-100; 50 mM Tris-HCl, pH 8.0; and 62.5 mM EDTA, pH 8.0). The solutions were mixed and incubated on ice for a further 5 to 10 minutes to lyse the cells. The lysed cells were centrifuged at approximately 38000 x g for 30 minutes at 4° C. and 8.0 ml of the supernatant was added to 8.4 g CsCl. Once the CsCl had dissolved, 1.0 ml of 5 mg/ml ethidium bromide solution was added, and the mixture was transferred to a 16×76 mm polyallomer tube (Beckman Instruments, Palo Alto, Calif. 94304). The tube was sealed, and centrifuged at ca. 185000 x g for 60 hours. The resulting plasmid band was visualized with ultraviolet light, and the DNA was removed using a syringe fitted with a 21-gauge needle. Ethidium bromide was removed from the DNA solution by several extractions with isopropanol that had been saturated with 5M NaCl. The recovered aqueous phase was dialysed against 3 changes of TE buffer for 1 hour each, extracted with buffered phenol/chloroform, extracted with chloroform and the DNA was precipitated by adding NaOAc and ethanol. The plasmid DNA (approximately 50 $\mu$g) was redissolved in 500 $\mu$l of TE. This plasmid was designated pCAR1; a restriction site map is shown in FIG. 3.

EXAMPLE 5

Construction of Plasmid pCAR6

Approximately 4 $\mu$g of plasmid pCAR1 (Example 4) were digested with HindIII at 37° C. for 3 hours in a HindIII digestion buffer. The digested DNA was fractionated on a 0.9% low-melting point agarose gel (Gibco-BRL) by electrophoresis in TBE buffer. The portion of the gel containing the approximately 12 kbp HindIII fragment was excised, melted by heating to 65° C. for 10 minutes, cooled to approximately 37° C. and extracted twice with buffered phenol (phenol buffered to a pH of approximately 7 with Tris-HCl, pH8.0). The recovered aqueous phase was extracted with buffered phenol/chloroform, extracted with chloroform, and treated with 0.1 volume 3M NaOAc and 2.5 volumes ethanol. The mixture was incubated at −20° C. for one hour to precipitate the DNA, which was pelleted by centrifugation in microcentrifuge tubes at 12000 x g for 5 minutes and redissolved in 20 $\mu$l of TE.

Approximately 0.6 $\mu$g of HindIII-digested, CIAP-treated pCP19 DNA (Example 2) and about 0.6 $\mu$g of the approximately 12 kbp HindIII fragment from pCAR1 (see above) were combined in a total volume of 20$\mu$l of DNA ligase buffer. One unit of T4 DNA ligase was added and the mixture was incubated at 12° C. for about 16 hours.

E. coli HB101 [H. Boyer and D.Roulland-Dussoix, Journal of Molecular Biology 41 (1969) 459] was grown in 50 ml of L-broth at 37° C. on a gyrotory incubator to an O.D. at 600 nm of approximately 0.5. The cells were pelleted by centrifugation at 1500 x g for 7 minutes at 4° C., resuspended in 4 ml 100 mM MgCl$_2$, repelleted, resuspended in 2 ml 100 mM CaCl$_2$, repelleted and resuspended again in 2 ml 100 mM CaCl$_2$. These cells were kept on ice for 1 hour. Transformation of the E. coli cells was performed as follows: 10 $\mu$l of the ligation reaction mixture was added to 200 $\mu$l of cells. The mixture was incubated on ice for 30 minutes, incubated at 42° C. for 2 minutes, added to 800 $\mu$l of L-broth and incubated at 37° C. for 30 minutes. Dilutions of this mixture were spread on L-agar plates supplemented with 10 $\mu$g ml$^{-1}$ tetracycline, and the plates were incubated at 37° C. for 16 hours. 20 tetracycline resistant colonies were restreaked on L-agar plates, supplemented with 10 $\mu$g ml$^{-1}$ tetracycline, and incubated overnight at 37° C. A loopful of cells was scraped from each plate and tested for carbamoylase activity using the 'phenol red test' described in Example 3. 15 of the 20 isolates gave positive tests for carbamoylase activity.

Plasmid DNA was isolated (on a small scale) from each of the 20 isolates as follows: Cells were scraped from a plate into 100 $\mu$l of 50 mM glucose, 25 mM Tris HCl pH8.0, 10 mM EDTA in a microcentrifuge tube, vortexed to mix and incubated at room temperature for 5 minutes. 200 $\mu$l of a fresh mixture of 0.2M NaOH and 1% sodium dodecyl sulphate was added, the tube was inverted to mix the contents and was incubated on ice for 5 minutes. 150 $\mu$l of 3M potassium acetate, adjusted to pH4.8 with acetic acid, was added to the tube, the contents were mixed by inverting the tube and the tube was incubated on ice for 5 minutes. The tube was centrifuged at 12000 x g for 2 minutes, the recovered supernatant was extracted with buffered phenol/chloroform, extracted with chloroform and the recovered aqueous phase was treated with 800 $\mu$l of cold (−20° C.) ethanol. The contents of the tube were mixed and incubated at room temperature for 2 minutes, the tube was centrifuged at 12000 x g for 2 minutes to pellet the nucleic acid. The pellet was dissolved in TE, and portions were used for restriction enzyme digestion to check the restriction map of the plasmid DNA. Of the 20 isolates tested, the 5 isolates that produced no carbamoylase enzyme contained pCP19 DNA, as judged from restriction enzyme digests of the plasmid DNA. All 15 that gave carbamoylase enzyme contained plasmid with the 12 kbp HindIII fragment from pCAR1. The plasmid DNA was one of two types, which differed only in the orientation of the 12 kbp HindIII fragment relative to the remainder of the plasmid vector. One of the isolates of E. coli with carbamoylase activity was incubated at 37° C. on a gyrotory incubator overnight in 400 ml L-broth supplemented with 10 $\mu$g ml$^{-1}$ tetracycline. Plasmid DNA was isolated from this culture using the method described in Example 4. This plasmid was designated pCAR6; a restriction site map is shown in FIG. 4.

EXAMPLE 6

Construction of Plasmid pCAR12

The plasmid vector pIJ2925 (FIG. 5) is similar to pUC18 (Norrander et al., Gene 26 (1983) 101–106), but it has a different polylinker at the multiple cloning site near the 5' end of the lacZ' gene. 2 $\mu$g of pIJ2925 DNA were digested with 10 units of BamHI (Gibco-BRL) at 37° C. for 3 hours in 100 $\mu$l of BamHI digestion buffer (50 mM Tris-HCl, pH8.0; 10 mM MgCl$_2$; 100 mM NaCl). One unit of CIAP was added and the incubation was continued for 30 minutes. 5 $\mu$l of 10% SDS were added and the mixture was incubated at approximately 68° C. for 15 minutes. The mixture was then cooled to room temperature, extracted with buffered phenol/chloroform, extracted with chloroform and precipitated by adding 0.1 volume 3M NaOAc and 2.5 volumes ethanol. After incubating at −20° C. for one hour the tube was centrifuged at 12000 x g for 5 minutes and the DNA pellet was redissolved in 10 $\mu$l TE.

About 20 $\mu$g of pCAR6 DNA was digested with 12 units of Sau3AI (Gibco-BRL) in Sau3AI digestion buffer (20 mM Tris HCl pH7.4, 5 mM MgCl$_2$, 50 mM KCl) at 37° C. for 1–30 minutes to obtain cleavage at some, but not all, of the recognition sites for the restriction enzyme. The progress of the digestion was monitored by removing aliquots and stopping the reaction by phenol/chloroform extraction. Portions of the DNA samples recovered were fractionated by electrophoresis on a 0.8% agarose gel in TBE buffer containing ethidium bromide and the DNA bands were visualised using ultraviolet light. DNA from one aliquot, in which most of the DNA fragments were in the size range 1 to 5 kbp, was precipitated using NaOAc and ethanol, and redissolved in 20 µl TE.

About 0.5 µg of BamHI-digested, CIAP-treated pIJ2925 DNA and about 1 µg of Sau3AI partially digested DNA of pCAR6 were mixed in 12 µl of DNA ligase buffer. One unit of T4 DNA ligase was added and the mixture was incubated at 12° C. for 16 hours.

A culture of E. coli DH5α (obtained from Gibco-BRL) was grown in a similar way to that described for E. coli HB101 in Example 5. The cells from this culture were treated with $MgCl_2$ and $CaCl_2$ and then transformed with the ligated DNA. Transformants were selected on L-agar plates containing 50 µl ml$^{-1}$ ampicillin, 12.5 µg ml$^{-1}$ isopropyl-β-D-galactopyranoside (IPTG, from Gibco-BRL) and 40 µg ml$^{-1}$ 5-bromo-4-chloro-3-indolyl-β-D galactopyranoside (X-gal, from Gibco-BRL). Approximately 300 'white' colonies, which failed to convert the X-gal to a blue compound and therefore presumably contain inserts in the polylinker of pIJ2925 which disrupt the lacZ' gene on the plasmid, were patched onto L-agar plates containing 50 µg ml$^{-1}$ ampicillin and grown overnight at 37° C. There were 25 patches per plate, and duplicate plates were made. One set of plates was used to test for carbamoylase enzyme activity using the method described in Example 3. Cells from 25 patches were tested in each tube; one of the 12 tubes gave a positive test. The colonies from the relevant duplicate plate were restreaked, grown overnight and tested individually for carbamyolase activity. One of the 25 clones gave a positive test; 400 ml of L-broth supplemented with 50 µg ml$^{-1}$ ampillicin was inoculated with a culture of this clone and then grown for about 20 hours in a gyrotory incubator at 37° C. Plasmid DNA was isolated from this culture using the method described in Example 4. This plasmid was designated pCAR12; a restriction map is shown in FIG. 6.

EXAMPLE 7

Construction of Plasmid pCAR21

Approximately 2 µg of plasmid pCAR12 (Example 6) were digested with 5 units of BglII (Gibco BRL) at 37° C. for 3 hours in BglII digestion buffer (50 mM Tris HCl pH8.0; 10 mM $MgCl_2$; 100 mM NaCl). The digested DNA was fractionated on a 0.9% low-melting point agarose gel by electrophoresis in TBE buffer. The portion of the gel containing the ca. 1.9 kbp BglII fragment was excised and the DNA was recovered using the method described in Example 5.

Approximately 0.5 µg of this DNA fragment was mixed with approximately 0.5 µg of BamHI-digested, CIAP-treated pIJ2925 DNA (Example 6) in a total volume of 12 µl of DNA ligase buffer. One unit of T4 DNA ligase was added, and the mixture was incubated at 12° C. for about 16 hours and then used to transform E. coli DH5α. The cells were spread on L-agar plates supplemented with ampicillin, IPTG and X-gal (Example 6) and incubated overnight at 37° C. 4 "white" colonies (see Example 6) were restreaked on L-agar plates containing ampicillin, IPTG and X-gal, grown overnight at 37° C. and small scale plasmid DNA preparations were performed on some of the cells, using the method described in Example 5. Portions of the DNA were digested with restriction enzymes to check the restriction map of the plasmids. 3 of the 4 clones tested contained a BglII fragment of aproximately 2 kbp, as expected from the ca. 1.9 kbp fragment from pCAR12 plus polylinker sequences from pIJ2925. Cells from these 3 clones were tested for carbamoylase activity using the "phenol red test" (Example 3). All of the tests were positive. 400 ml of L-broth containing 50 µg ml$^{-1}$ ampicillin was inoculated with a culture of one of the 3 "positive" clones and grown for about 20 hours in a gyrotory incubator at 37° C. Plasmid DNA was isolated from this culture using the method described in Example 4. This plasmid was designated pCAR21; a restriction map is shown in FIG. 7.

EXAMPLE 8

Construction of pCAR27 and pCAR28

Approximately 2 µg of plasmid pCAR21 were digested with 5 units of HindIII for 3 hours at 37° C. in HindIII digestion buffer. The digested DNA was fractionated on a 0.9% low-melting point agarose gel by electrophoresis in TBE buffer. The portion of the gel containing the ca. 1.9 kbp HindIII fragment was excised, the DNA was extracted using the method described in Example 5 and the DNA was dissolved in 20 µl TE.

Approximately 1 µg of M13mp19 [Norrander, Kempe and Messing; Gene 26 (1983) 101–106] replicative form (RF) DNA was digested with 5 units of HindIII for 3 hours at 37° C. in HindIII restriction buffer. The mixture was extracted with buffered phenol/chloroform, extracted with chloroform and the DNA was precipitated from the recovered aqueous phase using 3M NaOAc and ethanol. The DNA was collected by centrifugation and redissolved in 20 µl TE.

About 0.8 µg of HindIII-digested M13mp19 DNA and about 0.2 µg of the ca. 1.9 kbp HindIII fragment from pCAR21 were mixed in 15 µl of DNA ligase buffer. One unit of T4 DNA ligase was added and the mixture was incubated at 12° C. for 16 hours.

A culture of E. coli DH5αF' (obtained from Gibco-BRL) was grown in a similar way to that described for E. coli HB101 in Example 5. The cells from this culture were treated with $MgCl_2$ and $CaCl_2$ (as described in Example 5) and incubated on ice for 2 hours. Transfection of the E. coli cells was performed as follows: 0.5 µl or 4 µl of the ligation reaction mixture was added to 200 µl of cells, incubated on ice for 30 minutes, incubated at 42° C. for 2 minutes and incubated at room temperature for 15 minutes. 100 µl of an overnight culture of E. coli DH5α', 30 µl of 2% X-gal and 30 µl of 2.5% IPTG were added to the mixture of cells and DNA. This mixture was added to 2.5 ml of a 1:1 mixture of L-broth and L-agar (kept molten at 48°–50° C.), rapidly mixed and then poured onto an L-agar plate to produce a thin layer across the whole plate. The plate was incubated overnight at 37° C.

A mixture of blue (caused by β-galactosidase activity on X-gal) and "white" (i.e. not blue) plaques were visible on a lawn of DH5αF' cells. The HindIII site is within the lacZ' gene of M13mp19. Therefore insertion of DNA at this site should inactivate the lacZ' gene and thus inactivate β-galactosidase activity in DH5αF' cells infected with such M13mp19 derivatives. E. coli DH5αF' was grown in L-broth at 37° C. for about 16 hours. The resulting culture was diluted 1:100 with L-broth, and "white" plaques were inoculated into 1 ml of this diluted culture and incubated on a gyrotory incubator (ca. 300 rpm) for 5 hours. The cultures were transferred to microcentrifuge tubes and centrifuged at 12000 x g for 3 minutes to pellet the cells. The supernatants were stored at 4° C.; RF DNA was isolated from each sample of cells using the small-scale method for plasmid isolation described in Example 5. Restriction enzyme digests of these plasmids identified two isolates containing the ca. 1.9 kbp fragment from pCAR21, inserted in either orientation in M13mp19. 800 μl of the supernatant, from each of the cultures from which these plasmids were isolated, was inoculated separately into 400 ml of L-broth containing 4 ml of an overnight culture of E. coli DH5F'. The supernatants contain bacteriophage particles; these may infect the DH5αF' cells and produce double-stranded RF DNA inside the cells. Each of the 400 ml cultures was grown for 20 hours at 37° C. and treated as described in Example 4 to purify plasmid (RF) DNA. Restriction enzyme digests of the plasmids confirmed the structures of the plasmids. The plasmid from one culture was designated pCAR27 (FIG. 8), and the plasmid from the other culture was designated pCAR28 (FIG. 9).

EXAMPLE 9

Determination of the Nucleotide Sequence of the Agrobacterium DNA in pCAR27 and pCAR28

Plasmids pCAR27 and pCAR28 were treated similarly to produce nested sets of deleted clones and templates for sequencing:

Approximately 8 μg of RF DNA was digested with 10 units of KpnI and 10 units of BamHI in 100 μl of 20 mM Tris HCl pH7.4, 5 mM MgCl$_2$, 50 mM KCl. The DNA was purified using phenol/chloroform extraction and precipitated using ethanol in the presence of 0.3M NaOAc. The recovered DNA was treated with exonuclease III, using the method described by Henikoff (Gene 28 (1984) 351–359), to delete into the Agrobacterium DNA in the plasmids. The ligated products were used to transfect cells of E. coli DH5αF', using the method described in Example 8. Template DNA for use in sequencing reactions was prepared as follows:

"White" plaques were individually inoculated into 1 ml of a culture of E. coli DH5αF' (see Example 8), grown for 5–6 hours at 37° C. with vigorous shaking (300 rpm) and the cells were then pelleted by centrifugation. 800 μl of supernatant was removed to a fresh tube containing 150 μl of 20% polyethyleneglycol (PEG 6000), 2.5M NaCl, mixed and incubated at room temperature for 12 minutes. The tube was centrifuged at 12000 x g for 5 minutes to pellet the bacteriophage particles and the supernatant was discarded. The tube was centrifuged again briefly, all traces of supernatant were removed and the pellet was resuspended in 100 μl of 10 mM Tris-HCl (pH 8.0), 0.1 mM EDTA (pH8.0). 50 μl of phenol (buffered to pH7 with 100 mM Tris-HCl pH8.0) was added, mixed and the tube was incubated at room temperature for 5 minutes. The tube was centrifuged at 12000 x g for 3 minutes and the aqueous phase was removed to a fresh tube, extracted with chloroform and treated with NaOAc and ethanol to precipitate the DNA. The DNA was recovered by centrifugation and dissolved in 16 μl of water. This DNA is single-stranded DNA from M13 bacteriophage particles, and was used as the "template" for sequencing reactions. Sequencing was performed with Sequenase enzyme (United States Biochemical Corporation, Cleveland, Ohio, 44122, USA) using the method supplied with the kit containing the enzyme. Several templates were sequenced to obtain the complete sequence of the pCAR27 insert. Templates from deletions of pCAR28 were used to determine the sequence of the fragment in the opposite direction. The sequences from both directions were compared using software from DNASTAR Inc., Madison, Wis. 53715, USA to produce a consensus for the 1880 bp of Agrobacterium DNA; this consensus is shown in FIG. 10, together with the deduced amino acid sequence of the carbamoylase enzyme.

EXAMPLE 10

Construction of pCAR29

Approximately 2 μg of RF DNA of pCAR28 (Example 8; FIG. 9) was digested with 5 units of BspHI (New England Biolabs, Beverly Mass. 01915, USA) in 50 μl of 20 mM Tris HCl pH7.4, 5 mM MgCl$_2$, 50 mM KCl. The DNA was purified using phenol/chloroform extraction and chloroform extraction, precipitated using NaOAc and ethanol, recovered by centrifugation and redissolved in 40 μl of 10 mM Tris HCl pH7.4 10 mM MgCl$_2$, 50 mM NaCl, 50 μg ml$^{-1}$ bovine serum albumin, 10 mM 2-mercaptoethanol. 1 μl of a mixture of 250 μM deoxyguanosine-triphosphate, 250 μM deoxythymidinetriphosphate and 250 μM deoxycytidinetriphosphate was added followed by 2 units of "Klenow fragment" of E. coli DNA polymerase I (Gibco-BRL). The tube was incubated at 37° C. for 10 minutes, extracted with phenol/chloroform and extracted with chloroform. The recovered aqueous phase was treated with NaOAc and ethanol to precipitate the DNA, which was recovered by centrifugation and redissolved in 50 μl of 50 mM Tris-HCl pH8.0, 10 mM MgCl$_2$ and 50 mM NaCl. 5 units of each of the restriction enzymes HindIII and EcoRV (Gibco-BRL) were added, the contents of the tube mixed and the tube incubated at 37° C. for 3 hours. The digested DNA was fractionated on a 0.9% low melting point agarose gel by electrophoresis in TBE buffer. The portion of the gel containing the 990 bp fragment was excised and the DNA recovered from the agarose segment using the method described in Example 5. The DNA was redissolved in 20 μl of water.

pTR550 (FIG. 11) is a plasmid vector, constructed by Dr G. M. P. Lawrence (SmithKline Beecham Pharmaceuticals, Great Burgh, Epsom, Surrey, UK), and it is a derivative of pKK223-3 (Pharmacia LKB Biotechnology, S-751 82 Uppsala, Sweden). In pTR550 most of pKK223-3 that is derived from pBR322 has been replaced by DNA from pAT153. Approximately 1 μg of pTR550 was digested with 5 units of restriction enzyme SmaI (Gibco-BRL) in 30 μl of 20 mM Tris HCl pH.7.4, 5 mM MgCl$_2$, 50 mM KCl for 3 hours at 37° C. The digested DNA was purified using phenol/chloroform and chloroform extraction, precipitated using NaOAc and ethanol, recovered by centrifugation and redissolved in 30 μl of 50 mM Tris-HCl (pH8.0), 10 mM MgCl$_2$, 100 mM NaCl containing 5 units of HindIII. The mixture was incubated at 37° C. for 3 hours, extracted with phenol/chloroform, extracted with chloroform and the recovered aqueous phase was treated with NaOAc and ethanol to precipitate the DNA. The DNA was collected by centrifugation and redissolved in 20 μl of water.

Approximately 0.5 μg of pTR550 DNA, digested with both SmaI and HindIII, was mixed with approximately 0.2 μg of the 990 bp fragment (from the BspHI site at the beginning of the carbamoylase gene to the HindIII site at the end of the sequenced DNA) from pCAR28 in 20 μl of DNA ligase buffer. One unit of T4 DNA ligase was added and the mixture was incubated at 12° C. for about 16 hours.

A culture of E. coli JM101 (Messing, Recombinant DNA Technical Bulletin (NIH) 2 No 2 pp 43–48 (1979)) was grown, and the cells treated with CaCl$_2$ and MgCl$_2$, in a similar way to that described for *E. coli* HB101 in Example 5. The cells were transformed with the ligation mixture DNA as described in Example 5: dilutions of the cells were spread on L-agar plates containing 50 μg ml$^{-1}$ ampicillin and incubated overnight at 37° C. 22 ampicillin-resistant colonies were restreaked on L-agar plates containing 50 μg ml$^{-1}$ ampicillin, incubated at 37° C. overnight and then small-scale plasmid DNA preparations (using the method described in Example 5) were performed on cells of each of these isolates. Restriction enzymes digests of the DNA preparations indicated one plasmid of the desired construction. The isolate containing this plasmid was inoculated into 400 ml of L-broth containing 50 μg ml$^{-1}$ ampicillin, grown overnight on a gyrotory incubator at 37° C. and plasmid DNA was isolated using the method described in Example 4. Restriction enzyme digests confirmed the correct structure of this plasmid; the plasmid was designated pCAR29 (FIG. 12).

EXAMPLE 11

Expression of Carbamoylase in *E. coli* JM101 Containing pCAR29

*E. coli* JM101 containing pCAR29 (Example 10) was inoculated into 10 ml of L-broth containing 50 μg ml$^{-1}$ ampicillin and was grown overnight at 37° C. on a gyrotory incubator. 600 μl of this culture was inoculated into 60 ml of L-broth containing 50 μg ml$^{-1}$ ampicillin in a 250 ml conical flask and incubated on a gyrotory incubator at 37° C. After 2 hours (Optical density at 600 nm=ca.0.3) IPTG was added to a final concentration of 1 mM and growth was continued for a further 3 hours. The *E. coli* cells in the culture possessed carbamoylase activity. Cells of *E. coli* JM101 containing pTR550, grown in the way described above, did not possess any carbamoylase activity.

EXAMPLE 12

Transfer of pCAR1 from *E. coli* to Agrobacterium

Plasmid pCAR1 was transferred to Agrobacterium from *E. coli* by a triparental mating involving conjugation of the bacteria, with *E. coli* (pRK2013) as the 'helper strain' providing functions necessary for plasmid transfer. Agrobacterium 15-10 is a strain derived from Agrobacterium 80/44-2A by mutagenesis using ultra-violet light. A 10 ml culture of Agrobacterium 15-10 was grown in L-broth at 30° C. on a gyrotory incubator for approximately 20 hours. A 10 ml culture of *E. coli* AG1 (pCAR1)—see Example 3—was grown in L-broth containing 10 μg/ml tetracycline at 37° C. on a gyrotory incubator for approximately 16 hours. A 10 ml culture of *E. coli* HB101 (pRK2013)—see Figurski and Helinski, Proceedings of the National Academy of Science, USA 76 (1979) 1648–1652—was grown in L-broth containing 50 μg/ml kanamycin sulphate at 37° C. on a gyrotory incubator for approximately 16 hours. 800 μl of each culture was filtered through one sterile 0.45 μm pore-size HA filter (Millipore, Blackmoor Lane, Watford, WD1 8YW, U.K.). The filter, which retains the cells from the cultures, was then placed on the surface of an L-agar plate and was incubated for 24 hours at 30° C. The filter was removed from the surface of the plate to a screw-cap container containing 1 ml of sterile saline phosphate buffer and the container was shaken to re-suspend the cells from the filter. 100 μl of this solution, and dilutions in saline phosphate buffer, were plated on minimal medium (MM: 1 g KH$_2$PO$_4$, 1 g K$_2$HPO$_4$, 0.5 g MgSO$_4$.7H$_2$O, 0.1 g CaCl$_2$.2H$_2$O, 15 mg MnSO$_4$.4H$_2$O, 20 mg FeSO$_4$.7H$_2$O, 5 g glucose, 2 g (NH$_4$)$_2$SO$_4$ and 15 g agar, adjusted to pH7.0 with 5M NaOH) containing 100 μg/ml streptomycin sulphate and 10 μg/ml tetracycline. The *E. coli* parent strains should be unable to grow on MM containing 100 μg/ml streptomycin. Agrobacterium 15-10 should not grow in the presence of 10 μg/ml tetracycline. Therefore only pCAR1-containing Agrobacterium 15-10 cells should grow on this medium. After 5 days growth at 30° C. colonies were re-streaked on L-agar plates containing 25 μg/ml streptomycin sulphate and 10 μl/ml tetracycline and incubated at 30° C. for a further 3 days. Plasmid DNA was prepared from four isolates using the method described in Example 5. Restriction enzyme digestion of portions of the plasmid DNA was used to confirm that the tetracycline resistant ex-conjugants (i.e. progeny from the conjugation) did contain pCAR1.

EXAMPLE 13

Transfer of pCAR6 from *E. coli* to Agrobacterium

The method used for this transfer was very similar to that described for pCAR1 in Example 12. The parents in the mating were *E. coli* HB101 (pCAR6)—see Example 5, *E. coli* HB101 (pRK2013)—see Example 12—and Agrobacterium 15-10—see Example 12. Since both *E. coli* parent strains are auxotrophs, the progeny from the mating were plated on MM containing 10 μg/ml tetracycline, but no streptomycin, in order to select for Agrobacterium 15-10 (pCAR6) colonies. The presence of pCAR6 was confirmed by analysis of restriction enzyme digestion of plasmid DNA isolated from ex-conjugants.

EXAMPLE 14

Transfer of pCP19 from *E. coli* to Agrobacterium

The method used for this transfer was the same as that described for pCAR6 in Example 13, except that *E. coli* HB101 (pCP19) was a parent strain in the mating instead of *E. coli* HB101 (pCAR6). The presence of pCP19 in ex-conjugants was confirmed by analysis of restriction enzyme digestion of plasmid DNA isolated from ex-conjugants.

EXAMPLE 15

Demonstration of Extra Hydantoinase Activity Associated with pCAR1 and pCAR6

Agrobacterium 15-10 (pCAR1), Agrobacterium 15-10 (pCAR6) and Agrobacterium 15-10 (pCP19) were each inoculated into 50 ml of AJ-1 broth containing 0.1% alanine hydantoin and 10 μg/ml chloramphenicol and grown for 24 hours in a gyrotory incubator at 30° C. Each of the cultures was then treated as follows: the cells from 5 ml of culture were collected by centrifugation, and the wet weight of cells was measured. The cells were re-suspended in 20 ml of 1% D,L-5-(p-hydroxyphenyl) hydantoin in 0.2M Tris in a 50 ml screw-capped conical flask and shaken in a water bath at 42° C. Samples were removed after incubation for 10 minutes and after 30 minutes; the cells were spun out by centrifugation and the supernatant was assayed by HPLC for the presence of D-N-carbamoyl-p-hydroxyphenylglycine. The hydantoinase activity, in μmoles of product per g of cells (wet weight) per hour, was calculated using the difference between the amounts of D-N-carbamoyl-p-hydroxyphenylglycine product at 30 minutes and at 10 minutes. The hydantoinase activities for Agrobacterium 15-10 containing pCAR1 or pCAR6 were 5–6 times higher than the activity for Agrobacterium 15-10 containing pCP19, indicating that pCAR1 and pCAR6 contain the gene encoding hydantoinase activity.

EXAMPLE 16

Construction of Plasmid pCAR26

The plasmid vector pKT210 (Bagdasarian et al., Gene 16 (1981) pp237–247; map in FIG. 13) is a chloramphenicol-resistant derivative of the broad host range plasmid RSF1010. Approximately 2 µg of pKT210 DNA were digested with 5 units of EcoRI (Gibco-BRL) at 37° C. for 3 hours in EcoRI digestion buffer (50 mM, Tris-HCl, pH 8.0; 10 mM $MgCl_2$; 100 mM NaCl). A portion of the digestion mixture was analysed by electrophoresis; the digestion did not appear to be complete, but one unit of CIAP was added and the incubation was continued for 30 minutes. The digestion mixture was loaded onto a 0.9% low melting point agarose gel and the DNA was fractionated by electrophoresis in TBE buffer. The portion of the gel containing the ca. 11.4 kbp EcoRI fragment, corresponding to linearised plasmid DNA, was excised and the DNA was recovered using the method described in Example 5.

Approximately 2 µg of pCAR12 (Example 6; see also FIG. 6) were digested with 10 units of EcoRI at 37° C. for 3 hours in EcoRI digestion buffer. The digested DNA was fractionated on a 0.9% low melting point agarose gel by electrophoresis in TBE buffer. The portion of the gel containing the ca. 2.7 kbp EcoRI fragment was excised and the DNA was recovered using the method described in Example 5.

Approximately 0.5 µg of this ca. 2.7 kbp DNA fragment was mixed with approximately 0.5 µg of EcoRI-digested, CIAP-treated pKT210 DNA in a total volume of 12 µl of DNA ligase buffer. One unit of T4 DNA ligase was added and the mixture was incubated at 12° C. for about 16 hours.

A culture of E. coli AG1 (see Example 2) was grown in a similar way to that described for E. coli HB101 in Example 5. The cells from this culture were treated with $MgCl_2$ and $CaCl_2$ and then with the ligated DNA in a similar way to that described in Example 5. The cell-DNA mixture was spread on L-agar plates supplemented with 25 µg ml$^{-1}$ chloramphenicol, and the plates were incubated at 37° C. for 16 hours. 17 chloramphenicol-resistant transformants were restreaked on L-agar plates containing 25 µg ml-$^{1}$ chloramphenicol, and incubated overnight at 37° C. A loopful of cells of each transformant was scraped from the plate and resuspended in 600 µl of the "phenol red" assay buffer (Example 3). After incubation for 5 hours at 42° C., 3 of the reactions had developed a pink colour. Plasmid DNA was isolated, using the small-scale method described in Example 5, from the cultures corresponding to the pink coloration in the tests. Restriction enzyme digestion of the DNA preparations showed the presence of the ca. 2.7 kbp fragment from pCAR12. One of the plasmid preparations had two copies of the fragment from pCAR12; this plasmid was designated pCAR26. Further restriction enzyme digests showed that pCAR26 contained all of the Agrobacterium DNA from pCAR12 i.e. the fragment from pCAR12 extends beyond the EcoRI site in the carbamoylase gene (see FIGS. 6 and 10) to the EcoRI site in the polylinker. Therefore the isolated fragment (of ca. 2.7 kbp) must have come from partially digested pCAR12. A map of pCAR26 is shown in FIG. 14. Plasmid pCAR26 contains two copies of the complete carbamoylase gene.

EXAMPLE 17

Transfer of pCAR26 from E. coli to Agrobacterium

Like pCP19-derivatives, pKT210-based plasmids can be transferred by mating using the helper plasmid pRK2013. The method used for transfer of pCAR26 was similar to that described for pCAR1 in Example 12, but with the modifications described below. E. coli AG1 (pCAR26) was grown at 37° C. for 16 hours in L-broth containing 25 µg ml$^{-1}$ chloramphenicol; E. coli HB101 (pRK2013) and Agrobacterium 15-10 were grown as described in Example 12. Cells from these 3 cultures were filter-mated and then plated on MM containing 10 µg ml$^{-1}$ chloramphenicol. After 5 days growth colonies were restreaked on L-agar containing 25 µg ml$^{-1}$ streptomycin and 10 µg ml$^{-1}$ chloramphenicol and incubated at 30° C. for 3 days. Plasmid DNA was prepared from one isolate using the method described in Example 5. Restriction enzyme digestion of this DNA confirmed the presence of pCAR26.

EXAMPLE 18

Construction of Mobilisation-defective Derivative of pKT210

Approximately 2 µg of pKT210 were digested with 5 units of PflMI (New England Biolabs; c/o CP Laboratories P.O. Box 22 Bishop's Stortford, Herts CM23 3DH) in PflMI buffer (100 mM NaCl; 50 mM Tris-HCl, pH7.9; 10 mM $MgCl_2$; 1 mM dithiothreitol; 100 µg ml$^{-1}$ bovine serum albumin) at 37° C. for 16 hours. The digested DNA was fractionated on a 0.75% agarose gel by electrophoresis in TBE buffer. The portion of the gel corresponding to the 10.5 kb fragment was excised, and the DNA was recovered by electroelution using a Model UEA electroeluter (International Biotechnologies Inc. PO Box 9558 New Haven, Connecticut Conn. 06535), by conditions described in the apparatus manual, followed by precipitation with isopropanol and then centrifugation to collect the DNA. The DNA was redissolved in 32 µl of TE, 8 µl of a mixture of 150 mM sodium acetate (pH5.0), 250 mM NaCl, 5 mM zinc acetate, 25% glycerol were added, followed by 20 units of mung bean nuclease (New England Biolabs). This mixture was incubated at 37° C. for 30 minutes; this should generate blunt ends on the DNA fragment. The digested DNA was fractionated, and the 10.5 kbp fragment isolated, as described above. The DNA was redissolved in 20 µl of TE to which 5 µl of 5 x ligation buffer (Gibco-BRL) and one unit of T4 DNA ligase were added. The ligation mixture was incubated at 12° C. for 16 hours.

E. coli HB101 was transformed with 10 µl of the ligation mix as described in Example 5. Dilutions of this mixture were spread onto L-agar plates containing 25 µg ml$^{-1}$ of chloramphenicol. The plates were incubated at 37° C. for 48 hours; only a few transformants were obtained and these grew slowly on the initial selection plates. Sixteen colonies were restreaked onto L-agar plates containing 25 µg ml$^{-1}$ chloramphenicol and incubated for 16 hours at 37° C. after which the cells were scraped off and small-scale preparations performed using a modified version of the rapid boiling method (Holmes, D. S. and Quigley M. 1981. Anal. Biochem 114:p193). For each transformant, cells were resuspended in 300 µl STET (8% sucrose w/v; 0.5% Triton X-100 w/v; 50 mM EDTA; 50 mM Tris-HCl, pH8.0) in a microcentrifuge tube and 10 µl of 33 mg/ml of lysozyme in STET added. The suspension was incubated on ice for 30 minutes, and then placed in a boiling water bath for 3 minutes. The tube was centrifuged for 15 minutes and the pellet removed with a flat sided toothpick. The volume was corrected to 330 µl with STET and a further 330 µl of isopropanol was added. The tube was shaken to mix the contents, centrifuged for 10 minutes and the supernatant was discarded. The pellet was allowed to dry, then resuspended in 30 µl of TE. 2 µl portions were digested with restriction enzymes to determine the restriction map of each plasmid. DNA was digested with the restriction enzyme Acc1 (Gibco-BRL), in a total volume of 10 μl of restriction buffer React 3 (50 mM Tris-HCl, pH 8.0; 10 mM MgCl$_2$; 100 mM NaCl) containing 5 units of Acc1 for 2 hours at 37° C. Plasmid DNA from one of the clones appeared to have lost one of the Acc1 sites present in pKT210 (FIG. 13) indicating the loss of the larger (526 bp) PflMI fragment of pKT210 as expected. However on digestion of this plasmid, designated pWOR901, with PflMI it was found that only one of two PflMI fragments had been deleted, the smaller fragment remaining (FIG. 15). This was not expected and suggested that the fragment isolated from the PflMI digest must have included a fragment of approximately 10.9 kbp from a partial digest of pKT210 (FIG. 13). The frequency of transfer of pWOR901 in triparental matings (performed using a method similar to that described in Example 17) was found to be reduced by approximately $10^4$–$10^5$ compared with the frequency of transfer of pKT210. 500 ml of L-broth, supplemented with 25 μg ml$^{-1}$ chloramphenicol, was inoculated with the isolate of *E. coli* HB101 containing pWOR901 and incubated overnight at 37° C. on a gyrotory incubator. Plasmid DNA was isolated using the method in Example 4.

EXAMPLE 19

Electroporation of pWOR901 into Agrobacterium 15-10 and Isolation of pWOR902

Approximately 200 ng of pWOR901 DNA (Example 18) was used to transform Agrobacterium 15-10 by high voltage electroporation (Wen-jun.S. and Forde B. G. 1989. Nucleic Acids Research 17: p8385). The greatest efficiency occurred when a resistance of 600 ohms was applied. Transformants were selected on L-agar plates containing 10 μg ml$^{-1}$ chloramphenicol, grown at 30° C. for 4 days. Twenty-two small scale plasmid preparations were performed from cells of restreaked transformant colonies using the rapid boiling method described in Example 18. Restriction digests with 5 units Pst1 were performed on plasmid DNA in React 2 restriction buffer (50 mM Tris-HCl, pH 8.0; 10 mM MgCl$_2$; 50 mM NaCl) for 2 hours at 37° C. From these results various restriction patterns were observed. Examples of the different types of plasmid were used to transform *E. coli* HB101 (using the method of Example 5). Only one plasmid, when used to transform *E. coli*, gave stable chloramphenicol resistant colonies. Digests of plasmid DNA prepared from these chloramphenicol-resistant colonies showed that a further deletion of approximately 500 bp had occurred. This deletion completely removed the small PflMI fragment of pWOR901. The new plasmid was designated pWOR902. A large-scale preparation of DNA was performed on a 400 ml culture of *E. coli* HB101 (pWOR902). This DNA had no sites for PflMI (map shown in FIG. 16). After introduction by electroporation pWOR902 appeared to be stably maintained in Agrobacterium 15-10. Thus pWOR902 is a stable, mobilisation-deficient (Mob$^-$) derivative of pKT210, suitable for use in *E. coli* and in Agrobacterium. *E. coli* HB101 (pWOR902) was deposited at the National Collection of Industrial and Marine Bacteria, Aberdeen, Scotland on 4th Nov. 1991 under the accession number NCIMB 40451. The deposit was made under the Budapest Treaty on the deposition of micro-organisms for the purposes of patent procedure.

EXAMPLE 20

Construction of pCAR44 and Transfer to Agrobacterium

Approximately 2 μg of plasmid pCAR21 (Example 7) was digested with 5 units of HindIII at 37° C. for 3 hours in HindIII digestion buffer. The 1.9 kb fragment was isolated by electroelution from an agarose gel slice after fractionation by electrophoresis in TBE (Example 18). The recovered DNA was redissolved in 10 μl of TE.

Approximately 0.5 μg of pWOR902 (Example 19) was digested with HindIII, CIAP-treated and redissolved in 10 μl of TE. In an attempt to obtain multiple inserts an excess of fragment (from pCAR21) to vector was ligated: 0.1 μl of cut pWOR902 and 10 μl the 1.9 kb fragment were mixed in a total volume of 15 μl of ligation buffer (Gibco-BRL) containing 1 unit of T4 DNA ligase for approximately 16 hours at 12° C. 5 μl of the ligation mixture was used to transform *E. coli* HB101 (using a method similar to that described in Example 5) and the cells were spread on L-agar plates containing 25 μg ml$^{-1}$ chloramphenicol and incubated at 37° C. for 2 days. 24 transformants were restreaked on L-agar containing 25 μg ml$^{-1}$ chloramphenicol, grown overnight at 37° C., and then cells were scraped from the plate and used for small-scale plasmid preparations (Example 18). To determine the number of inserts, and their orientations, an EcoRI digestion was performed on an aliquot of DNA from each preparation. Analysis of the digested DNA showed that 5 of the clones contained double inserts of the fragment from pCAR21; all of these plasmids showed the same insert orientation, and this type of plasmid was designated pCAR44 (map in FIG. 17). 16 of the clones contained one insert of the pCAR21 fragment in pWOR902. A large scale plasmid preparation was performed on a 500 ml culture of one of the *E. coli* HB101 (pCAR44) isolates (method of Example 4) and 200 ng of this DNA was used to transform Agrobacterium 15-10 by electroporation (Example 19). Transformants were subjected to small-scale plasmid preparations; restriction enzyme digests confirmed the presence of pCAR44.

EXAMPLE 21

Demonstration of Extra Carbamoylase Activity Associated with pCAR26 and pCAR44 in Agrobacterium Agrobacterium 15-10 was inoculated into 50 ml of AJ-1 broth; Argobacterium 15-10 (pCAR26) and Agrobacterium 15-10 (pCAR44) were each inoculated into 50 ml of AJ-1 broth containing 10 μg ml$^{-1}$ chloramphenicol. All three cultures were grown for 24 hours in a gyrotory incubator at 30° C.; then each culture was treated as follows: 1.36 ml of culture broth was mixed in a microcentrifuge tube with 140 μl of 1% hexadecyltrimethylammonium bromide (in 65 mM Na$_2$HPO$_4$, 35 mM NaH$_2$PO$_4$, pH7.0) and incubated at room temperature for 10 minutes. 50 μl of this mixture was removed to a microcentrifuge tube containing 1.45 ml of 1.5% (w/v) D-N-carbamoyl-p-hydroxyphenylglycine in 65 mM Na$_2$HPO$_4$ 35 mM NaH$_2$PO$_4$ (pH7.0; readjusted to pH7.0 after dissolving the reaction substrate). The contents of the tube were mixed and incubated at 48° C. for 20 minutes. The cells were collected by centrifugation and the supernatant was analysed by HPLC for the presence of D(-)p-hydroxy phenyl glycine produced by the carbamoylase enzyme. The carbamoylase activities for Agrobacterium 15-10 containing pCAR26 or pCAR44, per ml of culture broth, were 10-30 times higher than the activity for Agrobacterium 15-10, presumably because the extra copies of the carbamoylase gene in the recombinant strains lead to more carbamoylase enzyme being produced.

EXAMPLE 22

Construction of pWOR903

Approximately 2 μg of pWOR902 DNA (Example 19) were digested with 10 units of Hind III at 37° C. for 15 hours in Hind III digestion buffer. The DNA was purified using phenol/chloroform extraction and chloroform extraction, precipitated using NaOAc and ethanol, recovered by centrifugation and redissolved in 40 μl of 10 mM Tris HCl pH7.4 10 mM MgCl$_2$, 50 mM NaCl, 50 μg m$^{-1}$ bovine serum albumin, 10 mM 2-mercaptoethanol. 1 μl of a mixture of 250 μM deoxyguanosine-triphosphate, 250 μM deoxythymidinetriphosphate and 250 μM deoxycytidinetriphosphate was added followed by 2 units of "Klenow fragment" of E. coli DNA polymerase I (Gibco-BRL). The tube was incubated at room temperature for one hour, extracted with phenol/chloroform and extracted with chloroform. The recovered aqueous phase was treated with NaOAc and ethanol to precipitate the DNA, which was recovered by centrifugation and redissolved in 15 μl of DNA ligase buffer. One unit of T4 DNA ligase was added and the mixture was incubated at 12° C. for about 16 hours.

5 μl of the ligation mixture was used to transform E. coli HB101 (using a method similar to that described in Example 5) and the cells were spread on L-agar plates containing 25 μg ml$^{-1}$ chloramphenicol and incubated at 37° C. for 2 days. 16 transformants were restreaked on L-agar containing 25 μg ml$^{-1}$ chloramphenicol, grown overnight at 37° C., and then cells were scraped from the plate and used for small-scale plasmid preparations (Example 18).

The object of this experiment was to fill-in the recessed ends generated by Hind III digestion to create blunt-ended DNA fragments. After religation this would remove the recognition sequence for Hind III. In order to determine whether this had occurred aliquots of DNA from the plasmid preparations were digested with Hind III. Further aliquots were digested with EcoRV. Most of the transformants appeared to contain plasmid with no Hind III sites but with similar EcoRV digestion patterns to pWOR902. A large scale plasmid preparation was performed a 500 ml culture of on one of these isolates (method of Example 4). This plasmid, pWOR903 (map shown in FIG. 18), has a restriction map like that of pWOR902 (FIG. 16) but it lacks the Hind III site.

EXAMPLE 23

Construction of pWOR904 and pWOR905

Approximately 1 μg of pWOR903 DNA (Example 22) was digested with 5 units of EcoRI at 37° C. for 3 hours in EcoRI buffer. The mixture was extracted with phenol/chloroform, extracted with chloroform and the DNA was recovered by precipitation with NaOAc and ethanol. The recovered DNA was dissolved in 50 μl of 50 mM Tris-HCl (pH8.0), 0.1 mM EDTA (pH8.0) containing 1 unit of CIAP. This phosphatase treatment, and recovery of the DNA, was as described in Example 2. The DNA was redissolved in 10 μl of water.

The plasmid pIC20R (Marsh et al Gene 32 (1984) pp481–485) is similar to the pUC plasmids (Vieira and Messing Gene 19 (1982) pp259–268) but with a modified polylinker. Approximately 2 μg of pIC20R DNA were digested with 5 units of EcoRI at 37° C. for about 15 hours in EcoRI buffer. The 84 bp fragment corresponding to the polylinker segment of pIC20R was recovered by electroelution from an agarose gel slice after fractionation by electrophoresis in TBE buffer (Example 18). The recovered DNA was redissolved in 10 μl of water.

8 μl of the 84 bp EcoRI fragment of pIC20R was mixed with 0.5 μl of the EcoRI-cut, CIAP-treated pWOR903 in a total volume of 12 μl of ligation buffer containing 1 unit of T4 DNA ligase for approximately 16 hours at 12° C. 5 μl of the ligation mixture was used to transform E. coli JM101 (using a method similar to that described in Example 5) and the cells were spread on L-agar plates containing 25 μg ml$^{-1}$ chloramphenicol and incubated at 37° C. for 2 days. 64 transformants were restreaked on L-agar containing 25 μg m$^{-1}$ chloramphenicol, grown overnight at 37° C., and then cells were scraped from the plate and used for small-scale plasmid preparations (Example 18).

Aliquots of the DNA preparations were digested with HindIII to detect the presence of the polylinker. Further digestions were performed with PstI, SstI, and double digests with BglII and SstII, to determine the orientation of the polylinker. Isolates containing the polylinker in either orientation were obtained; large scale plasmid preparations were performed on 500 ml cultures of one of each type of isolate (using the method of Example 4). Restriction maps of the plasmids, designated pWOR904 and pWOR905, are shown in FIGS. 19 and 20.

EXAMPLE 24

Construction of pCAR46 and Transfer to Agrobacterium

Approximately 2 μg of pCAR29 DNA (Example 10) were digested with 5 units of BamHI and 5 units of HindIII in a total of 50 μl of 50 mM Tris-HCl (pH8.0), 10 mM MgCl$_2$, 50 mM NaCl for 3 hours at 37° C. The 1.35 kb fragment was isolated by electroelution from an agarose gel slice after fractionation by electrophoresis (Example 18). The recovered DNA was redissolved in 10 μl TE.

Approximately 2 μg of pWOR904 DNA (Example 23) were digested with HindIII, followed by digestion with BglIII. The DNA was then treated with CIAP (Example 2) and finally redissolved in 10 μl TE.

1 μl of the cut pWOR904 was mixed with 4 μl of the 1.35 kb fragment of pCAR29 in a total volume of 12 μl of ligation buffer containing one unit of T4 DNA ligase and incubated at 12° C. for approximately 16 hours.

5 μl of the ligation mixture was used to transform E. coli DH5α (using a method similar to that described in Example 5) and the cells were spread on L-agar plates containing 25 μg ml$^{-1}$ chloramphenicol and incubated at 37° C. for 2 days. 15 transformants were restreaked on L-agar containing 25 μg ml$^{-1}$ chloramphenicol, grown overnight at 37° C., and then cells were scraped from the plate and used for small-scale plasmid preparations (Example 18).

Aliquots of DNA were digested with EcoRI, and with PstI, to confirm the presence of the insert derived from pCAR29. A large scale plasmid preparation was performed on a 500 ml culture of one of the isolates (using the method of Example 4). A restriction map of the plasmid, designated pCAR46, is shown in FIG. 21. 200 ng of this DNA was used to transform Agrobacterium 15-10 by electroporation (Example 19). Transformants were subjected to small scale plasmid preparations; restriction enzyme digests confirmed the presence of pCAR46. Agrobacterium 15-10 (pCAR46) was deposited at the National Collection of Industrial and Marine Bacteria, Aberdeen, Scotland on 14th Feb., 1992, under the accession number NCIMB 40478. The deposit was made under the Budapest Treaty on the deposition of micro-organisms for the purposes of patent procedure.

EXAMPLE 25

Demonstration of Extra Carbamoylase Activity Associated With pCAR46 in Agrobacterium Agrobacterium 15-10 was inoculated into 50 ml of AJ-1 broth; Agrobacterium 15-10 (pCAR46) was inoculated into 50 ml of AJ-1 broth containing 10 $\mu$g ml$^{-1}$ chloramphenicol. The cultures were grown for 24 hours in a gyrotory incubator at 30° C.; then each culture was treated as follows: 1.36 ml of culture broth was mixed in a microcentrifuge tube with 140 $\mu$l of 1% hexadecyltrimethylammonium bromide (in 65 mM Na$_2$HPO$_4$, 35 mM NaH$_2$PO$_4$, pH7.0) and incubated at room temperature for 10 minutes. 50 $\mu$l of this mixture was removed to a microcentrifuge tube containing 1.45 ml of 1.5% (w/v) D-N-carbamoyl-p-hydroxyphenylglycine in 65 mM Na$_2$HPO$_4$ 35 mM NaH$_2$PO$_4$ (pH7.0; readjusted to pH7.0 after dissolving the reaction substrate). The contents of the tube were mixed and incubated at 48° C. for 20 minutes. The cells were collected by centrifugation and the supernatant was analysed by HPLC for the presence of D(-)p-hydroxy phenyl glycine produced by the carbamoylase enzyme. The carbamoylase activity for Agrobacterium 15-10 containing pCAR46, per ml of culture broth, was 20–30 times higher than the activity for Agrobacterium 15-10.

EXAMPLE 26

Construction of pCAR31 and pCAR32

Approximately 2 $\mu$g of pCAR6 (Example 5) DNA were digested with 5 units of Cla I in a total of 50 ml of 50 mM Tris-HCl (pH 8.0), 10 mM MgCl$_2$ for 3 hours at 37° C. The digested DNA was fractionated on a 0.8% low melting point agarose gel by electrophoresis in TBE buffer. The portion of gel containing the ca. 4.7 kb Cla I fragment was excised and the DNA was recovered using the method described in Example 5.

Approximately 0.6 $\mu$g of Cla I digested, CIAP-treated pCP19 DNA (Example 2) and about 0.6 $\mu$g of the 4.7 kb Cla I fragment from pCAR6 were combined in a total volume of 20 $\mu$l of DNA ligase buffer. One unit of T4 DNA ligase was added and the mixture was incubated at 4° C. for about 16 hours.

10 $\mu$l of the ligation mix was used to transform *E. coli* DH5$\alpha$ (using a method similar to that described in Example 5) and the cells were spread on L-agar plates supplemented with 10 $\mu$g ml$^{-1}$ tetracycline and incubated overnight at 37° C. 18 tetracycline resistant colonies were restreaked on L-agar plates containing 10 $\mu$g ml$^{-1}$ tetracycline, incubated at 37° C. overnight and then small scale plasmid DNA preparations (using method described in Example 5) were performed on cells of each of these isolates. Restriction enzyme digests of the DNA preparations indicated clones with both orientations of the Cla I fragment in the vector were obtained. These vectors were designated pCAR31 and pCAR32 (FIGS. 22 and 23).

500 ml cultures of *E. coli* DH5$\alpha$ (pCAR31) and *E. coli* DH5$\alpha$ (pCAR32) were prepared in L-broth containing 10 $\mu$g ml$^{-1}$ tetracycline. Both cultures were treated as follows:

The culture was centrifuged at ca 6000 x g for 10 minutes at 4° C. and the resulting cell pellet was re-suspended in 10 ml of 50 mM glucose, 25 mM Tris-HCl (pH 8.0), 10 mM EDTA, 5 mg ml$^{-1}$ of lysozyme. The mixture was incubated at room temperature for 15 minutes. 10 mls of 0.2M NaOH, 1% SDS solution was added to the lysozyme treated cells and solutions were mixed and incubated on ice for 20 minutes. 15 mls of ice cold 3M potassium acetate (pH 5.8) was added to the reaction mixture and solutions were mixed and incubated on ice for a further 60 minutes. The lysed cells were centrifuged at approximately 38000 x g for 30 minutes at 4° C. The supernatants were collected and 0.6 volumes of isopropanol added and DNA allowed to precipitate for 15 minutes at room temperature. The reaction mixture was centrifuged at approximately 6000 x g for 30 minutes at room temperature and precipitated DNA re-suspended in 4.0 mls of TE. CsCl gradients were then prepared (as per Example 4) and plasmid DNA was re-dissolved in 500 $\mu$l of TE. Further restriction enzyme digestion of this DNA confirmed the correct structure of pCAR31 and pCAR32.

EXAMPLE 27

Transfer of pCAR31 and pCAR32 from *E. coli* to Agrobacterium pCAR31 and pCAR32 were transferred to Agrobacterium 15-10 by mating using the helper plasmid pRK2013 (as described for pCAR1 in Example 12). Plasmid DNA was prepared from isolates using the method described in Example 5. Restriction enzyme digestion of portions of the plasmid DNA was used to confirm that the tetracycline resistant ex-conjugants did contain either pCAR31 or pCAR32.

EXAMPLE 28

Demonstration of Extra Hydantoinase Activity Associated with pCAR31 and pCAR32

Agrobacterium 15-10 (pCAR1), Agrobacterium 15-10 (pCAR6), Agrobacterium 15-10 (pCAR26), Agrobacterium 15-10 (pCAR31), Agrobacterium 15-10 (pCAR32), and Agrobacterium 15-10 were each inoculated into separate flasks containing 50 mls of AJ-1 broth containing 0.1% alanine hydantoin and the appropriate antibiotic. The cultures were grown for 24 hours in a gyrotory incubator at 30° C. The resultant cultures were assayed for hydantoinase activity (as per Example 15). It was confirmed that pCAR1 and pCAR6, but not pCAR26, give increased hydantoinase activity in Agrobacterium 15-10. Strains containing pCAR31 or pCAR32 gave hydantoinase activities approximately 20 times higher than the activity for Agrobacterium 15-10 indicating that pCAR31 and pCAR32 contain the gene encoding hydantoinase activity.

EXAMPLE 29

Construction of pCAR36

Approximately 2 $\mu$g of pCAR31 (Example 26) DNA were digested with 5 units of Hind III in a total of 50 $\mu$l of 50 mM Tris-HCl (pH 8.0), 10 mM MgCl$_2$, 50 mM NaCl for 3 hours at 37° C. The digested DNA was fractionated on a 0.8% low melting point agarose gel by electrophoresis in TBE buffer. The portion of gel containing the ca 4.7 kb Hind III fragment was excised and the DNA was recovered using the method described in Example 5.

Approximately 0.6 $\mu$g of Hind III digested, CIAP treated pKT210 DNA (Example 16) and about 0.6 $\mu$g of the 4.7 kb Hind III fragment from pCAR31 were combined in a total volume of 20 $\mu$l of DNA ligase buffer. One unit of T4 DNA ligase was added and the mixture incubated at 4° C. for 16 hours.

10 $\mu$l of the ligation mix was used to transform *E.coli* HB101 competent cells (using a method similar to that described in Example 5) and the cells were spread on L-agar plates supplemented with 25 $\mu$g ml$^{-1}$ chloramphenicol. 17 chloramphenicol resistant colonies were re-streaked on L-agar plates containing 25 $\mu$g ml$^{-1}$ chloramphenicol, incubated at 37° C. overnight and then small scale plasmid DNA preparations (using the method described in Example 5)

were performed on cells of each of these isolates. Restriction enzyme digests confirmed the presence of pCAR36. A restriction digest map is shown in FIG. 24.

500 mls of L-broth supplemented with 25 μg ml$^{-1}$ chloramphenicol was inoculated with *E. coli* HB101 (pCAR36) and incubated overnight at 37° C. on a gyrotory incubator. Plasmid DNA was isolated using the method in Example 26.

EXAMPLE 30

Transfer of pCAR36 from *E. coli* to Agrobacterium pCAR36 was transferred to Agrobacterium by mating using the helper plasmid pRK2013 (as described for pCAR1 in Example 12). Plasmid DNA was prepared from isolates using the method described in Example 5. Restriction enzyme digestion of portions of the plasmid DNA was used to confirm that the chloramphenicol resistant ex-conjugants did contain pCAR36.

EXAMPLE 31

Demonstration of Extra Hydantoinase Activity Associated With pCAR36

Agrobacterium 15-10 and Agrobacterium 15-10 (pCAR36) were each inoculated into separate flasks containing 50 ml of AJ-1 broth containing 0.1% alanine hydantoin (plus 10 μg ml$^{-1}$ chloramphenicol for Agrobacterium 15-10 (pCAR36) culture), and grown for 24 hours in a gyrotory incubator at 30° C. The resultant cultures were assayed for hydantoinase activity (as per Example 15). The hydantoinase activities for Agrobacterium 15-10 containing pCAR36 were 6–7 times higher than the activity for Agrobacterium 15-10 confirming that pCAR36 contains the gene encoding hydantoinase activity.

EXAMPLE 32

Construction of pDAN3 and pDAN4

Approximately 2 μg of pCAR36 (Example 29) DNA were digested with 5 units of Sst I (SacI) in a total of 50 μl of 50 mM Tris-HCl (pH8.0), 10 mM MgCl$_2$, 50 mM NaCl for 3 hours at 37° C. The digested DNA was fractionated on a 0.8% low melting point agarose gel by electrophoresis in TBE buffer. The portion of the gel containing the ca 3.3 kb Sst I fragment was excised and the DNA as recovered using the method described in Example 5.

Approximately 0.5 μg of Sst I digested, CIAP treated pWOR902 DNA (Example 19) and 0.5 μg of the 3.3 kb Sst I fragment from pCAR36 were combined in a total volume of 20 μl of DNA ligase buffer. One unit of T4 DNA ligase was added and the mixture was incubated at 4° C. for 16 hours.

10 μl of the reaction mix was used to transform *E. coli* HB101 competent cells (using the method described in Example 5) and the cells were spread on L-agar plates supplemented with 25 μg ml$^{-1}$ chloramphenicol. 4 chloramphenicol resistant colonies were re-streaked on L-agar plates containing 25 μg ml$^{-1}$ chloramphenicol, incubated at 37° C. overnight and then small scale plasmid DNA preparations (using the method described in Example 5) were performed on cells of each of these isolates. Restriction enzyme digests of the DNA preparations indicated clones with either orientation of the Sst I fragment in the vector were obtained. These were designated pDAN3 and pDAN4 and restriction maps are shown in FIGS. 25 and 26.

500 mls of L-broth supplemented with 25 μg ml$^{-1}$ chloramphenicol was inoculated with *E. coli* HB101 (pDAN3) and a further 500 mls of L-broth supplemented with 25 μg ml$^{-1}$ chloramphenicol was inoculated with *E. coli* HB101 (pDAN4) and incubated overnight at 37° C. on a gyrotory incubator. Plasmid DNA was isolated using the method described in Example 26.

EXAMPLE 33

Electroporation of pDAN3 and pDAN4 into Agrobacterium

Approximately 200 ng of either pDAN3 or pDAN4 was used to transform Agrobacterium 15-10 by electroporation (Example 19). Transformants were subjected to small scale plasmid preparations; restriction enzyme digests confirmed the presence of pDAN3 and pDAN4.

EXAMPLE 34

Demonstration of Extra Hydantoinase Activity Associated With pDAN3 and pDAN4

Agrobacterium 15-10 (pCAR36), Agrobacterium 15-10 (pWOR902), Agrobacterium 15-10 (pDAN3) and Agrobacterium 15-10 (pDAN4) were each inoculated into separate flasks containing 50 ml of AJ1 medium (Example 1), supplemented with 5 g l$^{-1}$ (NH$_4$)$_2$SO$_4$ and 10 μg ml$^{-1}$ chloramphenicol, and grown for 24 hours at 30° C. Each of the cultures were then treated as follows: 500 μl of 1M MnSO$_4$ solution was added to the culture which was then shaken at 30° C. for a further 35 minutes. The broth was assayed in the following way: 1360 μl of broth either neat or diluted was added to 140 μl of 1% cetyltrimethylammonium bromide solution in an eppendorf tube, mixed and incubated at room temperature for 5 minutes. 1 ml of this solution was added to 19 mls of 1% D, L-5-(p hydroxyphenyl) hydantoin in 0.2M Tris in a 50 ml screw capped conical flask and shaken in a water bath at 42° C. Samples were removed after incubation for 10 minutes and 30 minutes and assayed using an HPLC (Example 15). The hydantoinase activity in μmoles of product per ml of cells per hour was calculated.

It was demonstrated that pCAR36, pDAN3 and pDAN4 give increased hydantoinase activity in Agrobacterium 15-10. Strains containing pDAN4 gave hydantoinase activities approximately 230 times higher than the activity for Agrobacterium 15-10 containing pWOR902.

EXAMPLE 35

Construction of pGal2789RS3Carb

A copy number mutant of the naturally occurring *E. coli* plasmid NR1 was obtained by spontaneous mutation. This plasmid (pRR21) was then reduced in size by deleting un-needed regions to yield pDPT 2789. This is a 125 copy plasmid containing the inc F11 region and Chloramphenicol and Spectinomycin resistance markers. pDPT2789 was then cut with NdeI, filled in and religated to make pDTP2789 (Nde$^-$). pDPT2789 (Nde$^-$) was then digested with Stu1 and Esp1 and a Stu1-Esp1 fragment containing a Pga1 promoter with a synthetic ribosome binding site downstream was inserted. This vector was called pGal2789RS3V1V2.

pGal2789RS3V1V2 was digested with NdeI, filled-in with Klenow, and then digested with BamH1. pCAR21 (Example 7) was digested with BspH1, filled-in with Klenow, and then digested with BamH1. These digestions released an ~900 bp fragment containing the sequences coding for the carbamoylase gene resulting in the plasmid pGal2789RS3Carb that expresses the carbamoylase gene off the Gal promoter.

This plasmid was then transformed into a number of *E. coli* K12 host strains by standard CaCl₂ procedures and production of carbamoylase was monitored during cell growth by Coomassie blue staining of SDS-PAGE gels on which total cell extracts had been run.

---

We claim:

1. An isolated DNA endogenous to Agrobacterium 80/44-2A, said DNA encoding a carbamoylase enzyme said enzyme having the capability of converting a D-N-carbamoyl (optionally substituted phenyl) glycine into the corresponding D-(optionally substituted phenyl) glycine and encoding a hydantoinase enzyme which enzyme has the ability to convert a D,L-(optionally substituted phenyl) hydantoin into the corresponding D-N-carbamoyl (optionally substituted phenyl) glycine.

2. An isolated DNA according to claim 1 obtained from Agrobacterium 80-44/2A.

3. Recombinant DNA vector comprising the DNA of claim 1.

4. A host cell which has been transformed with the recombinant DNA of claim 3.

5. A host cell transformed with the vector of claim 3.

6. A transformed host cell according to claim 5, wherein said host cell is selected from the group consisting of Agrobacterium and *E. coli*.

7. A method of producing carbamoylase and/or hydantoinase activity in a host cell, said method comprising the steps of:
   (a) introducing into said host cell the vector as defined in claim 3; and
   (b) culturing said host cell transformed in step (a) under conditions sufficient to produce said carbamoylase and/or hydantoinase activity.

8. An isolated DNA molecule comprising a nucleotide sequence encoding the amino acid sequence set forth in SEQ ID NO: 2.

9. A recombinant vector comprising the DNA of claim 8.

10. A host cell transformed with the vector of claim 9.

11. A transformed host cell according to claim 10, wherein said host cell is selected from the group consisting of Agrobacterium and *E.coli*.

12. An isolated DNA molecule comprising the coding region of SEQ ID NO: 1.

13. A recombinant vector comprising the DNA of claim 12.

14. A host cell transformed with the vector of claim 13.

15. A transformed host cell according to claim 14, wherein said host cell is selected from the group consisting of Agrobacterium and E.coli.

16. A recombinant DNA vector selected from the group consisting of:
   pCAR1 (having the configuration of restriction sites in FIG. 3),
   pCAR6 (having the configuration of restriction sites in FIG. 4),
   pCAR12 (having the configuration of restriction sites in FIG. 6),
   pCAR21 (having the configuration of restriction sites in FIG. 7),
   pCAR26 (having the configuration of restriction sites in FIG. 14),
   pCAR27 (having the configuration of restriction sites in FIG. 8 ),
   pCAR28 (having the configuration of restriction sites in FIG. 9),
   pCAR29 (having the configuration of restriction sites in FIG. 12),
   pCAR31 (having the configuration of restriction sites in FIG. 22),
   pCAR32 (having the configuration of restriction sites in FIG. 23),
   pCAR36 (having the configuration of restriction sites in FIG. 24),
   pCAR44 (having the configuration of restriction sites in FIG. 17), and
   pCAR46 (having the configuration of restriction sites in FIG. 21).

17. A host cell which has been transformed with the recombinant DNA vector of claim 16.

18. A transformed host cell according to claim 17, in which the host cell is selected from the group consisting of Agrobacterium and E. coli.

19. A method of producing carbamoylase activity in a host cell, said method comprising the steps of:
   (a) introducing into said host cell a vector as defined in claim 16; and
   (b) culturing said host cell transformed in step (a) under conditions sufficient to produce said carbamoylase activity.

20. A recombinant DNA vector selected from the group consisting of pCAR1, pCAR6, pCAR31, pCAR32, and pCAR36.

21. A host cell which has been transformed with the recombinant DNA vector of claim 20.

22. A transformed host cell according to claim 21, in which the host cell is selected from the group consisting of Agrobacterium and E. coli.

23. A method of producing carbamoylase and/or hydantoinase activity in an Agrobacterium host cell, said method comprising the steps of:
   (a) introducing into said host cell a vector as defined in claim 20; and
   (b) culturing said host cell transformed in step (a) under conditions sufficient to produce said carbamoylase and/or hydantoinase activity.

24. A recombinant DNA vector selected from the group consisting of pDAN3 (having the configuration of restriction sites in FIG. 25) and pDAN4 (having the configuration of restriction sites in FIG. 26).

25. A host cell which has been transformed with the recombinant DNA vector of claim 24.

26. A transformed host cell according to claim 25, in which the host cell is selected from the group consisting of Agrobacterium and E. coli.

27. A method of producing hydantoinase activity in a host cell, said method comprising the steps of:
   (a) introducing into said host cell a vector as defined in claim 26; and
   (b) culturing said host cell transformed in step (a) under conditions sufficient to produce said hydantoinase activity.

28. A process for the production of a carbamoylase enzyme, said process comprising the step of:
   expressing in an Agrobacterium host recombinant DNA endogenous to Agrobacterium 80/44-2A, said DNA encoding a carbamoylase enzyme.

29. A process for the production of a carbamoylase enzyme, said process comprising the step of:
   expressing in a host cell DNA comprising a nucleotide sequence encoding the amino acid sequence set forth in SEQ ID NO: 2.

30. The process according to claim 29, wherein the host is Agrobacterium.

31. A method of producing carbamoylase activity in a host cell, said method comprising the steps of:
   (a) introducing into said host cell DNA comprising the coding region of SEQ ID NO: 1 or a carbamoylase-encoding portion thereof in a vector selected from the group consisting of pWOR902 (NCIMB 40451) having the configuration of restriction sites in FIG. 16, pWOR903 having the configuration of restriction sites in FIG. 18, pWOR904 having the configuration of restriction sites in FIG. 19, pWOR905 having the configuration of restriction sites in FIG. 20 wherein said DNA is positioned for expression within said vector; and
   (b) culturing said host cell transformed in step (a) under conditions sufficient to produce said carbamoylase activity.

32. A process for the production of a carbamoylase enzyme, said process comprising the step of:
   expressing in a host cell DNA comprising the coding region of SEQ ID NO: 1.

33. The process as claimed in claim 32, wherein the host cell is Agrobacterium.

34. An isolated carbamoylase enzyme comprising the amino acid sequence set forth in SEQ ID NO: 2.

35. A polypeptide sequence comprising the amino acid sequence set forth in SEQ ID NO: 2.

36. An isolated carbamoylase enzyme encoded for by a nucleotide sequence comprising the coding region of SEQ ID NO: 1.

37. A carbamoylase enzyme according to claim 36, obtained by expressing recombinant DNA encoding said enzyme in Agrobacterium.

38. An isolated hydantoinase enzyme encoded by a vector selected from the group consisting of pDAN3 and pDAN4.

39. An isolated DNA comprising a hydantoinase coding portion of a vector selected from the group consisting of pDAN3 and pDAN4.

40. A recombinant vector comprising the DNA of claim 39.

41. A host cell transformed with the vector of claim 40.

42. A transformed host cell according to claim 41, wherein said host cell is selected from the group consisting of Agrobacterium and E.coli.

43. A method of producing hydantoinase activity in a host cell, said method comprising the steps of:
   (a) introducing into said host cell a vector as defined in claim 41; and
   (b) culturing said host cell transformed in step (a) under conditions sufficient to produce said carbamoylase and/or hydantoinase activity.

44. A method of producing hydantoinase activity in a host cell, said method comprising the steps of:
   (a) introducing into said host cell DNA comprising the hydantoinase encoding portion of a vector selected from the group consisting of pDAN3 and pDAN4 in a vector selected from the group consisting of pWOR902 (NCIMB 40451) having the configuration of restriction sites in FIG. 16, pWOR903 having the configuration of restriction sites in FIG. 18, pWOR904 having the configuration of restriction sites in FIG. 19, PWOR905 having the configuration of restriction sites in FIG. 20 wherein said DNA is positioned for expression within said vector; and
   (b) culturing said host cell transformed in step (a) under conditions sufficient to produce said hydantoinase activity.

45. A vector selected from the group consisting of pWOR902 (NCIMB 40451) having the configuration of restriction sites in FIG. 16, pWOR903 having the configuration of restriction sites in FIG. 18, pWOR904 having the configuration of restriction sites in FIG. 19, pWOR905 having the configuration of restriction sites in FIG. 20. thereof.

* * * * *

UNITED STATES PATENT AND TRADEMARK OFFICE
CERTIFICATE OF CORRECTION

PATENT NO. : 5,858,759
DATED : January 12, 1999
INVENTOR(S) : Neal, et al.

It is certified that error appears in the above-identified patent and that said Letters Patent is hereby corrected as shown below:

Column 1, lines 4-5 should be deleted and replaced with--

This application is a file wrapper continuation application of U.S. Application No. 08/356,369, now abandoned which was the National Stage of International Application No. PCT/GB93/01378, filed on Jun. 30, 1993. --.

Column 3, line 62, delete "Figure 10 shows" and insert --Figures 10A, 10B-1 and 10B-2 show--.

In the Claims:

In Claim 43, page 37, line 15, please delete "carbamoylase and/or".

UNITED STATES PATENT AND TRADEMARK OFFICE
CERTIFICATE OF CORRECTION

PATENT NO. : 5,858,759
DATED : January 12, 1999
INVENTOR(S) : Neal, et al.

It is certified that error appears in the above-identified patent and that said Letters Patent is hereby corrected as shown below:

In Other Publications:

On page 1, please amend "Rurser et al., Biotechnol. Let. 12:259-264 (1990)" to read "Runser et al., Biotechnol. Let. 12:259-264" 1990.

Signed and Sealed this

Twenty-second Day of February, 2000

Attest:

Q. TODD DICKINSON

Attesting Officer

Commissioner of Patents and Trademarks